US012778676B2

(12) United States Patent
Vinokour et al.

(10) Patent No.: US 12,778,676 B2
(45) Date of Patent: *Nov. 3, 2026

(54) LASER SYSTEM AND METHOD FOR DETECTING AND PROCESSING INFORMATION

(71) Applicant: Terra Quantum AG, St. Gallen (CH)

(72) Inventors: Valerii Vinokour, St. Gallen (CH); Emil Sobol, St. Gallen (CH)

(73) Assignee: Terra Quantum AG, St. Gallen (CH)

( * ) Notice: Subject to any disclaimer, the term of this patent is extended or adjusted under 35 U.S.C. 154(b) by 311 days.

This patent is subject to a terminal disclaimer.

(21) Appl. No.: 18/370,858

(22) Filed: Sep. 20, 2023

(65) Prior Publication Data

US 2024/0130789 A1 Apr. 25, 2024

(30) Foreign Application Priority Data

Sep. 23, 2022 (EP) .................................... 22197529

(51) Int. Cl.
*A61B 18/26* (2006.01)
*A61B 18/00* (2006.01)
*A61B 18/22* (2006.01)

(52) U.S. Cl.
CPC ...... *A61B 18/26* (2013.01); *A61B 2018/0022* (2013.01); *A61B 2018/00404* (2013.01);
(Continued)

(58) Field of Classification Search
None
See application file for complete search history.

(56) References Cited

U.S. PATENT DOCUMENTS 8,535,298 B1 * 9/2013 Neev .................... A61B 18/245 606/7
9,125,677 B2 * 9/2015 Sobol .................. A61B 5/4839
(Continued)

FOREIGN PATENT DOCUMENTS

CN 114074231 A * 2/2022 ........... B23K 26/382
EP 1665997 B1 12/2011
(Continued)

OTHER PUBLICATIONS

Clarivate Analytics, translation of CN-114074231-A (Year: 2026).*
(Continued)

*Primary Examiner* — Manolis Pahakis
(74) *Attorney, Agent, or Firm* — Fitch Even Tabin & Flannery LLP

(57) ABSTRACT

A laser system suitable for modification of a calcified blood vessel includes a laser source, a feedback controller configured to regulate a dosimetry of the laser source to produce spatially and/or temporally modulated laser light, a catheter comprising a first optical delivery element, the first optical delivery element configured to guide the modulated laser light to an in-vivo object in the blood vessel, and a detecting element, configured to detect one or more physical, chemical, mechanical and/or dimensional characteristics of an area of the in-vivo object in real-time, wherein the feedback controller is configured to process the real-time detected information pertaining to the one or more physical, chemical, mechanical and/or dimensional characteristics of the area in real-time, wherein the feedback controller is further configured to regulate the dosimetry of the laser source for a controlled formation of a porous structure and/or a zone of denaturized tissue in the in-vivo object.

7 Claims, 12 Drawing Sheets

(52) U.S. Cl.
CPC ............... *A61B 2018/00648* (2013.01); *A61B 2018/00702* (2013.01); *A61B 2018/00744* (2013.01); *A61B 2018/00791* (2013.01); *A61B 2018/2211* (2013.01)

(56) References Cited

U.S. PATENT DOCUMENTS

| | | | | |
|---|---|---|---|---|
| 9,242,005 | B1* | 1/2016 | Hossainy | A61K 47/42 |
| 2003/0036751 | A1* | 2/2003 | Anderson | A61B 5/0059 606/9 |
| 2005/0251116 | A1* | 11/2005 | Steinke | A61B 5/0066 606/14 |
| 2010/0076299 | A1 | 3/2010 | Gustus et al. | |
| 2012/0283557 | A1* | 11/2012 | Berlin | A61F 9/00825 600/407 |
| 2013/0190613 | A1* | 7/2013 | Boppart | A61N 7/00 600/427 |
| 2016/0184021 | A1 | 6/2016 | Kowalewski et al. | |
| 2016/0184526 | A1* | 6/2016 | Beyar | A61M 25/104 604/500 |
| 2016/0317226 | A1* | 11/2016 | Jagdeo | A61B 90/06 |
| 2017/0220754 | A1* | 8/2017 | Harrah | A61B 18/26 |
| 2018/0323571 | A1* | 11/2018 | Brown | A61B 18/20 |
| 2020/0397312 | A1* | 12/2020 | Ben Oren | A61B 5/02007 |
| 2021/0038310 | A1* | 2/2021 | Bukesov | A61B 18/24 |
| 2021/0038311 | A1* | 2/2021 | Shelton | A61B 18/26 |
| 2022/0183756 | A1* | 6/2022 | Milner | A61B 18/24 |
| 2024/0099771 | A1* | 3/2024 | Sobol | A61L 27/3654 |
| 2024/0099888 | A1* | 3/2024 | Sobol | A61L 27/3654 |

FOREIGN PATENT DOCUMENTS

| | | | |
|---|---|---|---|
| WO | WO 2019/070782 | A1 | 4/2019 |
| WO | WO 2021/255013 | A1 | 12/2021 |

OTHER PUBLICATIONS

Sobol et al., "Laser-induced micropore formation and modification of cartilage structure in osteoarthritis healing." *J. of Biomedical Optics*, 22(9): 11 pp. (Sep. 2017).

European Patent Office, Extended European Search Report in European Patent Application No. 22197529.5, 7 pp. (Mar. 21, 2023).

* cited by examiner

LASER SYSTEM AND METHOD FOR DETECTING AND PROCESSING INFORMATION

CROSS-REFERENCE TO RELATED APPLICATIONS

The instant application claims priority to European Patent Application No. 22197529.5, filed Sep. 23, 2022, which is incorporated herein in its entirety by reference.

FIELD OF THE DISCLOSURE

The present disclosure concerns the field of medical laser technology. In particular, the disclosure relates to a laser system that may be applied in an endovascular surgery.

BACKGROUND OF THE INVENTION

Coronary heart disease has a globally leading mortality rate. About 20.1 million adults in the USA aged 20 and older have coronary artery disease (CAD). Nowadays, the percutaneous coronary intervention (PCI) is a key method for the treatment of coronary heart disease. One of the most important causes of the disease is the structural change in the vessel walls due to age, causing the vessels to become more rigid. This results in a formation of calcified plaques. A major challenge of the modern cardiology is partial decalcification, to increase the compliance of the aorta and arteries. Modern therapeutic and surgical methods provide only temporary effect and are often accompanied by undesirable side effects. The population burden of the peripheral artery disease (PAD) is estimated to be 8.5 million in the USA and over 200 million worldwide. Thus, the treatment of the PAD is of special relevance.

Modern methods to treat calcified arteries include high-pressure non-compliant balloons (generating pressure up to 10 atm), ultrahigh-pressure balloons (generating a pressure up to 40 atm), cutting balloons, and various forms of atherectomy, which are all designed to facilitate PCI in severely calcified coronary arteries. Balloon-based techniques, often applied in a balloon angioplasty, do not remove calcium but aim to increase plaque elasticity and allow stent expansion by cracking calcified plaques in one or multiple areas. The intravascular lithotripsy (IVL) system (Shockwave Medical) is a novel balloon catheter-based device that utilizes pulsatile mechanical energy to disrupt calcified lesions. The disadvantages of the IVL are associated with the side effects due to the possible tearing of the vessel walls by high pressure and recalcification of the arteries, which can occur more than six months after treatment. One of the problems to be solved is the treatment of chronic total occlusions (CTO), in particular the CTO of peripheral arteries. Femoropopliteal chronic total occlusions (FP-CTOs) are encountered in 40% to 50% of patients presenting for endovascular management of symptomatic peripheral artery disease. However, even with experienced clinicians, a long occlusion with a heavy calcium burden can make crossing the FP-CTO challenging, which is why they are associated with a crossing failure rate as high as 30%.

Restenosis occurs as a result of tissue growth at the spot of treatment and can be viewed as a result of the treatment following the localized trauma of angioplasty. According to the 2020 National Cardiovascular Registry report, the intracoronary stent restenosis (ICS) arises in 10.6% of the PCI procedures. To prevent restenosis, drug-eluting stents (DES) are used, but they help only in case of a fast (less than 6 months) follow-up, and for late follow-ups (18 months) the rate of restenosis is higher. One of the reasons of recalcification and restenosis is a residue stress which is usually due to two factors: (i) a pathological alteration in structure and composition of the vessel wall, and (ii) a plastic deformation running in the course of stenting, cardio lithotripsy and other intravascular procedures. The residue stress therefore is one of the important factors of restenosis after many cardio interventions, including stenting.

A combination of laser and balloon is known to be used to treat calcified blood vessels. For example, optical boring is used for reducing a size of calcified plaques in a blood vessel and a balloon is expanded to widen the narrowed pathway.

Conventional methods use invasive laser/ultrasonic conditions (for example lasers generating local temperatures of over 300° C.), possibly damaging not only the calcified plaques but also other tissues in a blood vessel. Moreover, for conventional methods, the calcified plaques are untreated and rigid, thus a large pressure of the balloon is needed, increasing the hazard of further damaging the blood vessel. Further, after the operation, residue stress is generated on the blood vessel wall, which leads to a recalcification of the blood vessel. In a technical view, due to the destructive nature of the conventional method, an ideal effect cannot be achieved after a single surgery, thereby reducing the resource efficiency of the treatment.

WO 2019/070782 A1 discloses a device for treating a patient with a coronary artery chronic total occlusion (CTO) which includes a combination of imaging, tissue ablation, and tissue removal capabilities.

US 2022/0 183 756 A1 discloses an apparatus, systems and methods for fracturing calcium in an artery of a patient using a combination of a laser and a balloon.

EP1665997B1 discloses a method for generating a spatially and temporally modulated laser light.

Sobol, Emil, et al. "Laser-induced micropore formation and modification of cartilage structure in osteoarthritis healing." Journal of biomedical optics 22.9 (2017): 091515 discloses a laser induced micropore structure formation.

BRIEF SUMMARY OF THE INVENTION

The present disclosure describes a device and a method that solve one or more of the above-mentioned problems of the prior art.

A first aspect of the disclosure provides a laser system suitable for modification of a calcified blood vessel, comprising: a laser source; a feedback controller, configured to regulate a dosimetry of the laser source to produce spatially and/or temporally modulated laser light; a catheter comprising a first optical delivery element, the first optical delivery element configured to guide the modulated laser light to an in-vivo object in the blood vessel; and a detecting element, configured to detect one or more physical, chemical, mechanical and/or dimensional characteristics of an area of the in-vivo object in real-time, wherein the feedback controller is configured to process the real-time detected information pertaining to the one or more physical, chemical, mechanical and/or dimensional characteristics of the area in real-time, wherein the feedback controller is further configured to regulate in real-time the dosimetry of the laser source based on the real-time-detected information for a controlled formation of a porous structure and/or a zone of denaturized tissue in the in-vivo object.

Traditional methods for ablating a calcified plaque usually only control a total power of a laser or ultrasonic energy exerted on the calcified plaque and observe only an initial state, which is a complete calcified plaque, and a final state, which is an ablated calcified plaque. This method is inefficient and produces extra damage to the human body. In the present disclosure, the real-time regulated laser system may monitor a local environment and use a real-time feedback method. This may facilitate a controlled modification of certain properties of the blood vessel (such as compliance and elasticity of the blood vessel) with reduced or no negative influence on the surrounding tissues. In one embodiment where a calcified plaque need not be ablated, the treatment may soften the calcified plaque, so that it may be deformed under less pressure and/or deformed without abrupt fracturing of the calcified plaque. For example, this effect may be achieved while a blood vessel lumen area is being expanded by a balloon or a stent. A porous structure can further increase the drug transportation and can prevent recalcification and restenosis of the blood vessels. In another embodiment where a calcified plaque should be destroyed, for example in case of the CTO, the present disclosure may facilitate a more efficient laser ablation with a less damage to the blood vessel. The porous structure can be filled with water, which may enhance the interaction between the calcified plaque and the modulated laser light because of the enhanced water content in the porous structure. This can enhance the laser ablation efficiency of the calcified plaque. In yet another embodiment, the method can be further applied to reduce a residue stress on a vessel wall. In this embodiment, the modulated laser light may induce intermolecular bond breaking and may lead to denaturation of fibrous tissue instead of/or in addition to the porous structure formation. Through a real-time feedback regulation, the whole procedure may become smoother and can be optimized to different conditions. The new method may be efficient, controllable, may produce less damage to the environment, and may have a wide range of applications.

For instance, a medical doctor or a medical practitioner may introduce the catheter to the vicinity of a to-be treated blood vessel area manually. The doctor or practitioner may then select a function of the laser system, for example to determine whether to perform a laser ablation or a laser induced stress relaxation and start the laser treatment. After the laser treatment is started, it can run automatically until a detected information reaches a predetermined threshold, for example, when the stress of the in-vivo object is reduced to a predetermined value or when the size of the in-vivo object is reduced to a predetermined value. When such threshold is reached, the laser system can either stop the laser treatment or pause and wait for the next command of the doctor or the practitioner.

In conclusion, the present disclosure may provide a solution using a real-time controlled laser based on feedback information reflecting the treatment environment and may realize a non-invasive mild laser treatment condition. This may reduce the damage to the blood vessel.

BRIEF DESCRIPTION OF THE SEVERAL VIEWS OF THE DRAWING(S)

To illustrate the technical features of embodiments of the present disclosure more clearly, the accompanying drawings provided for describing the embodiments are introduced briefly in the following. The accompanying drawings in the following description are merely some embodiments of the present disclosure, and modifications of these embodiments are possible without departing from the scope of the present disclosure as defined in the claims.

DETAILED DESCRIPTION OF THE INVENTION

The following description presents examples of the implementation of the present disclosure, and the scope of the present disclosure, but the disclosure is not limited to presented examples. Any variations or replacements can be easily made by persons skilled in the art. Accordingly, the scope of protection of the present disclosure is defined by the attached claims.

Figure 1:
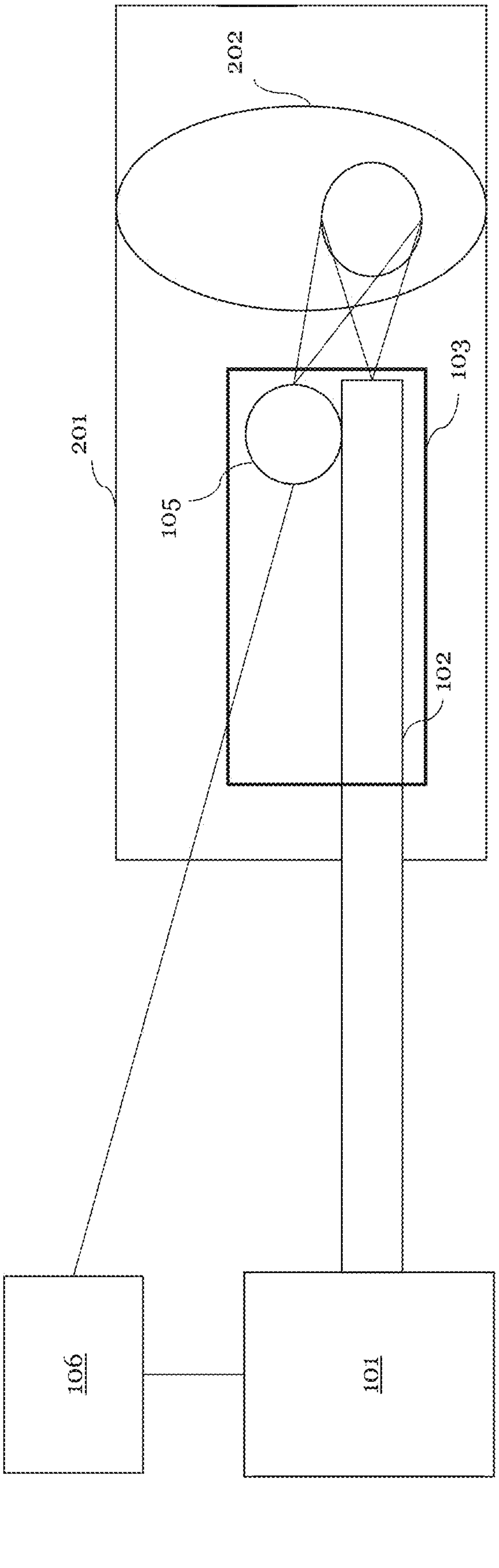
FIG. 1 is a schematic illustration of a laser system according to an embodiment.

FIG. 1 is a schematic illustration of a laser system disclosed by the present disclosure. The laser system is suitable for modification of a calcified blood vessel 201. The laser system comprises: a laser source 101; a feedback controller 106, configured to regulate a dosimetry of the laser source 101 to produce spatially and/or temporally modulated laser light; a catheter 103 comprising a first optical delivery element 102, the first optical delivery element 102 configured to guide the modulated laser light to an in-vivo object 202 in the blood vessel 201; and a detecting element 105, configured to detect one or more physical, chemical, mechanical and/or dimensional characteristics of an area of the in-vivo object 202 in real-time, wherein the feedback controller 106 is configured to process the real-time-detected information pertaining to the one or more physical, chemical, mechanical and/or dimensional characteristics of the area in real-time, wherein the feedback controller 106 is configured to regulate in real-time the dosimetry of the laser source 101 based on the real-time-detected information for a controlled formation of a porous structure and/or a zone of denaturized tissue in the in-vivo object.

Figure 2:
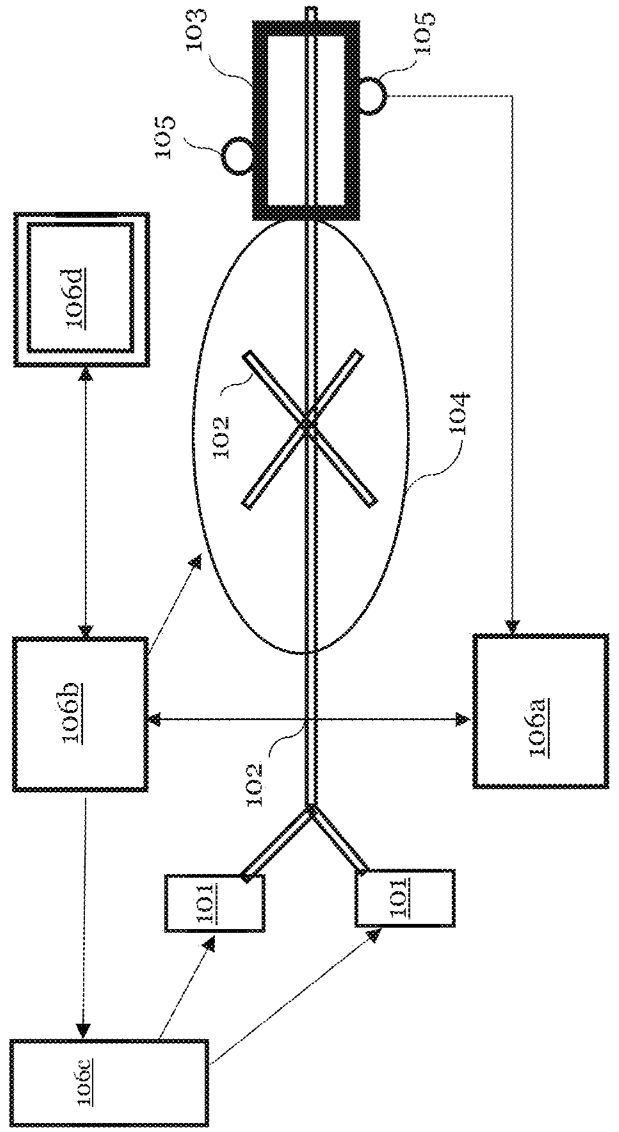
FIG. 2 is a schematic illustration of a laser system according to an embodiment.

FIG. 2 is a schematic illustration of a laser system according to an embodiment.

The laser system may comprise a diagnostic element 106*a*, configured to receive a detected information and process the detected information. The diagnostic element 106*a* comprises a User Interface, configured to present the detected information to a user, e.g., a researcher or a medical doctor. For example, the User Interface may be configured to present a stress distribution of an area of the in-vivo object 202. The diagnostic element 106*a* may send the detected information unprocessed to a remote high-performance computer, the remote hybrid computational facility, and/or the remote quantum computer 106*d*. The diagnostic element 106*a* may further be configured to preprocess the detected information. For example, the diagnostic element 106*a* may be configured to analyze a detected information pertaining to a scattered light and determine a size distribution of pores in a porous structure. The laser system may further comprise a feedback control element 106*b*, configured to manage a data flow in the laser system. The data flow may comprise a flow of real-time detected information pertaining to a temperature and a mechanical property of an area of the in-vivo object; a flow of processed/preprocessed detected information; a command generated for regulating a dosimetry of a laser source 101. The feedback control element 106*b* may be configured to control the direction and a sequence of the data flow, so that the irradiation of the laser source 101 can be modulated in real-time based on real-time detected information. The laser system may further comprise a radiation modulation element 106*c*, configured to modulate the radiation of the laser 101 source temporally and spatially. The radiation modulation element 106*c* may be configured to receive a command generated for modulating the radiation of the laser 101 and regulate a dosimetry of the laser source 101, or the radiation modulation element 106*c* may be configured to receive the dosimetry value directly from the external high-performance computer, the remote hybrid computational facility, and/or the remote quantum computer 106*d*. The laser system may further comprise an external high-performance computer, a remote hybrid computational facility, and/or a remote quantum computer 106*d* configured to process the detected information or the preprocessed detected information to generate a command for modulating the radiation of the laser source 101 or to regulate a dosimetry of the laser source 101. The external high-performance computer, the remote hybrid computational facility, and/or the remote quantum computer 106 may be configured to solve a thermal equation, a thermo-mechanical equation, a mechanical equation, and an equation of motion within a small, time interval, for example within a millisecond up to several minutes, so that the method for treating a calcified blood vessel according to the present disclosure can be carried out continuously. The diagnostic element 106*a*, the feedback control element 106*b*, the radiation modulation element 106*c* and the high-performance computer, the remote hybrid computational facility, and/or the remote quantum computer 106*d* may be parts of the feedback controller 106 in FIG. 1. Although FIG. 2 shows a separation of the diagnostic element 106*a*, the feedback control element 106*b*, the radiation modulation element 106*c* and the remote ultra-fast computer 106*d*, this separation should not be interpreted as a physical separation but rather a separation of their logical functions. The feedback controller 106 may also refer to a combination of one or more of the diagnostic elements 106*a*, the feedback control element 106*b*, the radiation modulation element 106*c* and the high-performance computer, the remote hybrid computational facility, and/or the remote quantum computer 106*d*. For example, if the feedback controller 106 is only configured to process the detected information pertaining to a temperature and a stress by a processor to acquire a characteristic about a porous structure and a zone of a denaturized tissue on an in-vivo object. The diagnostic element 106*a* alone or a combination of the diagnostic element 106*a* and the high-performance computer, the remote hybrid computational facility, and/or the remote quantum computer 106*d* can be seen as a feedback controller 106. In this case, the feedback controller 106 facilitates an evaluation of a porous structure and a zone of denaturized tissue on an in-vivo object and an initialization of parameters for the laser source 101. For example, if the feedback controller 106 is further configured to process the detected information in real-time during the porous structure formation and the formation of a zone of the denaturized tissue induced by the temporally and spatially modulated radiation of the laser source 101. A combination of the feedback control element 106*b* and the diagnostic element 106*a* can be seen as a feedback controller 106. In this case, the feedback controller 106 facilitates a monitoring of the laser-induced stress relaxation and molding of the calcified plaque or the lithotripsy (ablation) of the chronic total occlusion (CTO). For example, a doctor can decide on their own when to interrupt the laser irradiation depending on whether the size distribution of pores in the porous structure reaches a predetermined threshold.

The laser system may comprise a laser 101, configured in a way that its radiation be spatially and temporally modulated by the feedback controller 106. Spatial modulation may refer to varying a location, a shape of the laser beam and the laser-illuminated area and a certain intensity distribution of the laser-induced light in the laser illuminated area. To realize such a spatial modulation, the laser system may comprise one or more lasers sources 101. FIG. 2 only shows two laser sources 101, yet a laser system according to the present disclosure may comprise more laser sources 101. A plurality of lasers 101 may facilitate a complicated spatial modulation of laser irradiation. A spatial modulation may also be realized through a combination of one or more lasers with other auxiliary passive elements, such as lenses, mirrors, an optical splitter and other optical systems thereof. Each one of the lasers 101 may implement an independent temporally modulated irradiation. A temporally modulated laser irradiation is usually a sequence of pulses of laser irradiation with variable pulse repetition rate, pulse duration, pulse intensities or other variable attributes of a laser pulse. A temporal modulated laser radiation may also refer to non-pulsed laser radiation with a variable shape in the time domain and a variable shape in the frequency domain. The irradiation of the laser sources 101 may be real-time modulated. A real-time modulation may correspond to a constantly regulating a dosimetry of the laser source 101, regulating the dosimetry upon receiving a signal from the feedback controller 106 or updating the laser dosimetry after a certain number of pulses in a sequence. A laser source 101 in the present disclosure may be a combination of several types of lasers, including a solid state laser (for example a NdYag laser or a Holmium laser) and/or a diode laser.

The laser system may further comprise an optical delivery system 102, configured to deliver the modulated laser radiation or laser light to a target. The optical delivery system 102 can be an optical fiber, a bundle of optical fibers or other types of optical delivery elements. The optical delivery system 102 may also be configured to deliver other laser signals, for example a probing laser signal for detecting a certain property in a blood vessel 201. In an exemplary embodiment, laser modulation may take into account the possible distortion of the laser signal due to propagation in the laser delivery system 102 and implement corresponding compensations. The optical delivery system 102 may comprise an optical out-coupler for delivering the laser signals in a form of laser irradiation to the target. In an embodiment, for example in the cold lithotripsy method as will be illustrated in detail later, the optical out-coupler may be configured to physically contact an in-vivo object 202 without exerting damage on them.

The laser system may further comprise one or more detecting elements 105. The detecting elements 105 are configured to detect one or more physical, chemical, mechanical and/or dimensional characteristics of the in-vivo object 202 in the blood vessel 201. The one or more physical, chemical, mechanical and/or dimensional characteristics may comprise a temperature, a stress, the size and the number of pores, thermomechanical characteristics, optical characteristics, electrical characteristics, and other characteristics characterizing the environment of the in-vivo object 202 and the status of the in-vivo object itself. The characteristics may be detected in a direct and in an indirect way. For example, the detecting element 105 may comprise a conductivity measuring element, configured to measure a conductivity of a blood vessel. This characteristic can then be feedbacked as an electrical signal. In another example, the detecting element 105 may comprise an optical receiving element, configured to receive a scattered light. The scattered light can be feedbacked as an optical signal and be processed to deliver the information about a temperature, a stress, a size distribution of gas bubbles, and a size distribution of pores, based on the characteristics of the optical signal such as, for example but not restricted to, wavelength distribution and an angular intensity distribution. In an exemplary embodiment, the detecting element 105 may comprise a conventional diagnostic device, such as one of the following: an X-Ray; a CT; an Ultrasonography (US); a Doppler US; an MRI; an Intravascular ultrasound (IVUS); an OCT; an OCE; a Multispectral Optoacoustic tomography (MSOT); a fluorescence molecular tomography (FMT); and acoustic tomography. In particular, an IVUS allows to detect calcium, an OCT allows for measuring dimensions of the target and the OCE measures the stress and mechanical properties. The IVUS is a widely available clinical tool for guiding percutaneous interventions and intraluminal imaging. While the IVUS uses frequencies from 20 to 40 MHz and provides fair penetration depth, it lacks the sufficient resolution, having the resolution restricted to ~120 mm, necessary for studying the thin-cap thrombus, atheroma lesions, and other possible fine details of the vasculature. Conversely, while the OCT provides the high resolution of about 2-20 mm for tomographic visualization of the coronary arteries, its maximal penetration depth is only about 2-3 mm Because the IVUS waves penetrate deeper into the media and adventitia, the OCT may be combined with the IVUS modalities which enhances and improves a quantitative analysis of the characteristics of the in-vivo object significantly. It is understood from this embodiment, that it may be advantageous to combine the different types of detecting elements 105 comprising conventional diagnostic devices for acquiring a more detailed picture of the in-vivo object and of the environment of the in-vivo object in a blood vessel. This improvement can lead to an increased data volume to be processed. In an exemplary embodiment, the performance of the remote high-performance computer, a remote hybrid computational facility, and/or a remote quantum computer 106*d* should be high enough to ensure implementing a real-time modulation of the laser irradiation.

Figure 3:
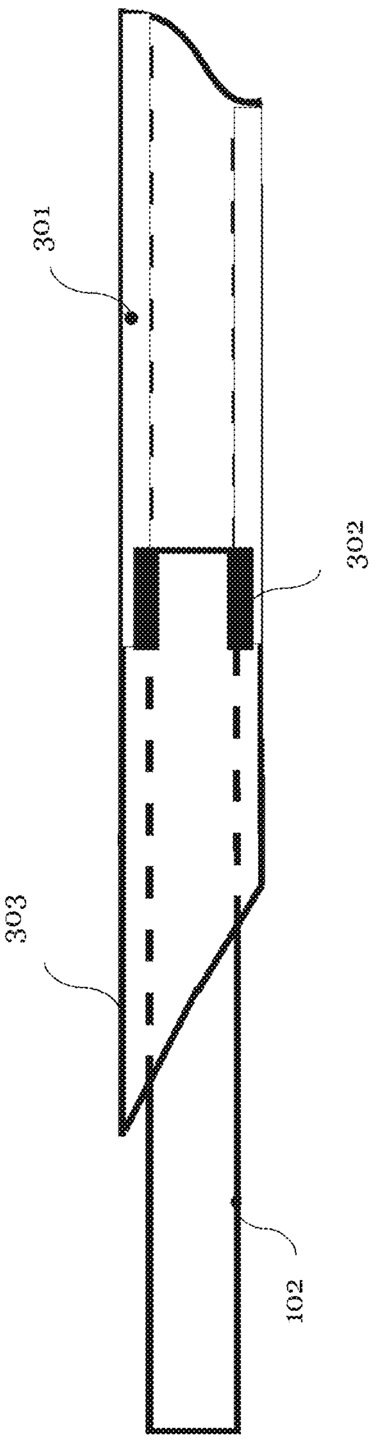
FIG. 3 is a schematic illustration of a catheter according to an embodiment.

The laser system further comprises a catheter 103 configured to carry an end of the optical delivery element 102 and the detecting element 105 in a blood vessel 201 to the vicinity of the in-vivo object 202. The catheter 103 may be configured to make fine position adjustment in the blood vessel 201 and record the position of the laser light exerted on the target or a position of the information detected by the detecting element 105, such that a precise spatial modulation of the laser signal and an acquisition of spatial distribution of the detected information is realized. In an exemplary embodiment, the catheter 103 may further comprise and be attached to a servo element for a precise position control. An example of the catheter 103 comprising a detecting element measuring electrical conductivity, is illustrated in FIG. 3. The catheter 103 may comprise a coating 301, a conductive adhesive 302 and a metal tip 303.

The laser system may further comprise a balloon 104 configured to be inflated to expand a lumen area in the blood vessel 201. The balloon 104 may be configured to be modulated by the controller 106 as well. For example, the balloon 104 may be configured to be inflated during the laser treatment. The balloon 104 may be configured to be inflated after a laser induced stress relaxation. The controller may be configured to modulate the balloon 104 and the laser 101 simultaneously for different purposes. For example, for molding of a calcified plaque, the balloon may be inflated simultaneously during a laser irradiation. For another example, for a minimum pressure required for the balloon 104, the balloon may be inflated only after the laser softening of the calcified plaque.

Figure 4:
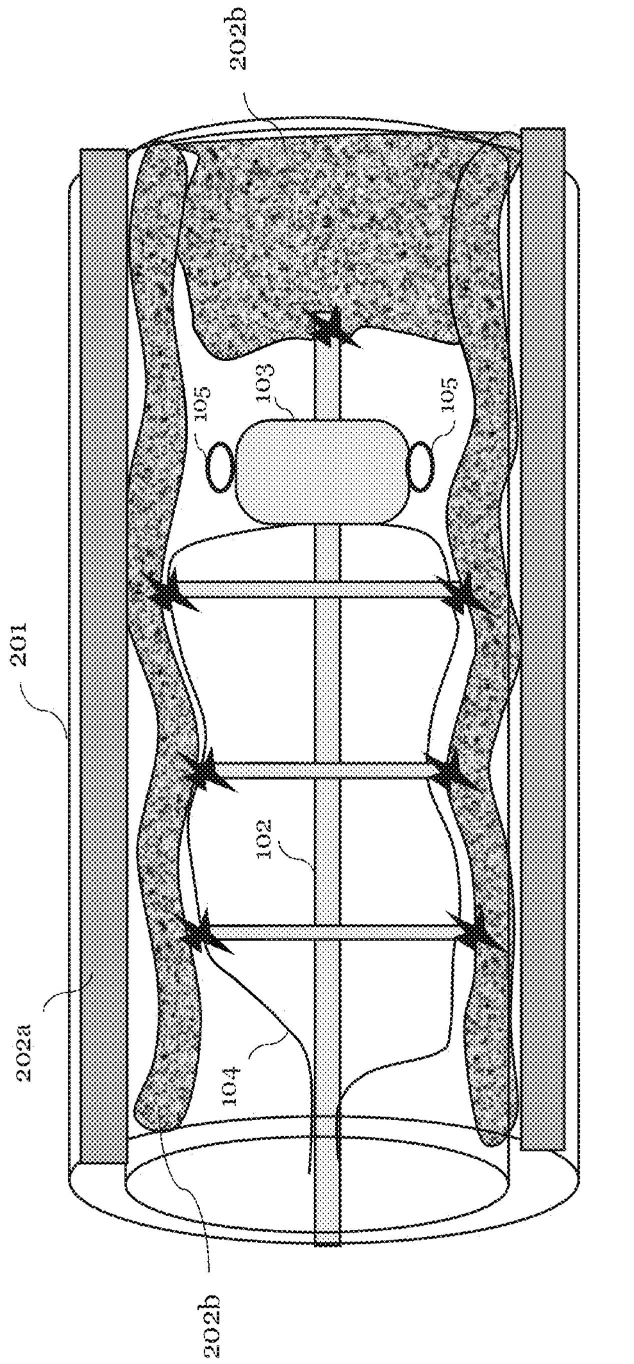
FIG. 4 is a schematic illustration of a laser system in operation according to an embodiment.

FIG. 4 is a schematic illustration of a laser system in operation according to an embodiment. The blood vessel 201 subject to the treatment suffers from the imposed calcified plaques 202*b*. The calcified plaque 202*b* is expectedly attached to or located at the vessel wall 202*a*. The calcified plaque 202*b* may further restrict a lumen area of the blood vessel 201 significantly, so that the pathway available for the blood flow is reduced. In the case illustrated in FIG. 4 the calcified plaque 202*b* on the right-hand side totally blocks the pathway of the blood flow, which is typical in a CTO. To treat and cure the blood vessel 201, the large piece of the calcified plaque 202*b* on the right-hand side of FIG. 4 needs to be destroyed. According to the present disclosure, the regulated laser source 101 can be used to generate temporal porous structures within the calcified plaque 202*b* facilitating a more efficient laser ablation of the calcified plaque 202*b*. This approach is called the "cold lithotripsy". After the calcified plaque 202*b* causing the total occlusion is destroyed, or have its volume reduced through implementing the cold lithotripsy, the laser source 101 with the modulated radiation may be further configured to form a stabilized porous structure and zones of denaturized tissues within the calcified plaque 202*b* attached to the vessel wall 202*a* for softening the calcified plaque 202*b* and reduce a mechanical stress developing in it without destroying it. After or during the mechanical stress relaxation in and softening of the calcified plaque 202*b* attached to the vessel wall 202*a*, a balloon 104 can be inflated to expand a lumen area of the blood vessel 201. Compared to the conventional method, the balloon 104 used after a laser induced softening of the calcified plaque 202*b* and stress relaxation may require less pressure, producing less damage to the environment, including the vessel wall 202*a*. After the laser treatment is concluded, the modulated radiation of the laser source 101 may further be configured to reduce a residue stress on the vessel wall 202*a*. This can minimize a chance of recalcification and restenosis of the blood vessel 201.

Figure 5:
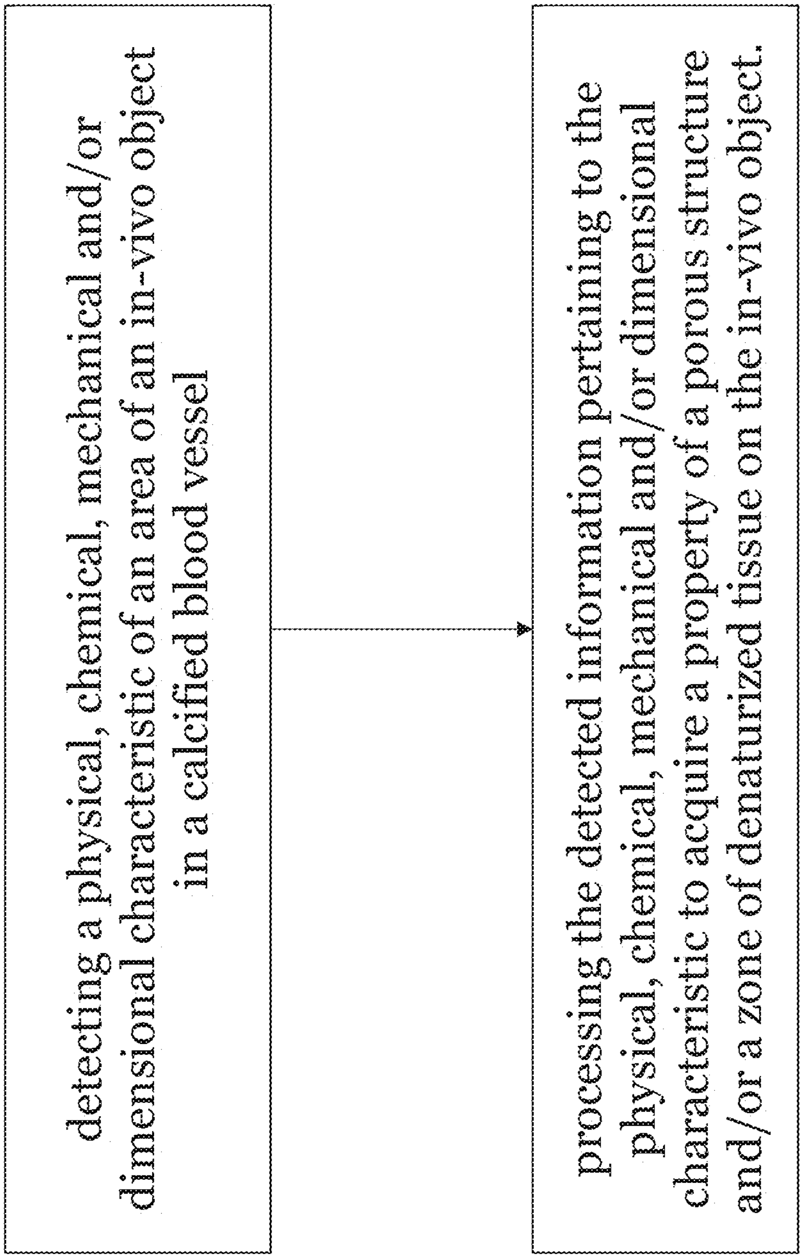
FIG. 5 is a flow chart illustrating a method for detecting and processing information according to an embodiment.

FIG. 5 is a flow chart illustrating a method for detecting and processing information according to an embodiment. In this embodiment, the method comprises:

a) detecting a physical, chemical, mechanical and/or dimensional characteristic of an area of an in-vivo object in a calcified blood vessel;

b) processing the detected information pertaining to the physical, chemical, mechanical and/or dimensional characteristic to acquire a property of a porous structure and/or a zone of denaturized tissue on the in-vivo object.

As outlined above, the method illustrated in FIG. 5 may be used to evaluate a porous structure and a zone of the denaturized tissue. This structural evaluation may be carried out for initializing a working condition of the laser. This method may be further used to monitor and evaluate an effect of the modulated laser radiation on the in-vivo object. This laser effect evaluation may be carried out for controlling laser effect or damage induced by the laser on the in-vivo object.

Figure 6:
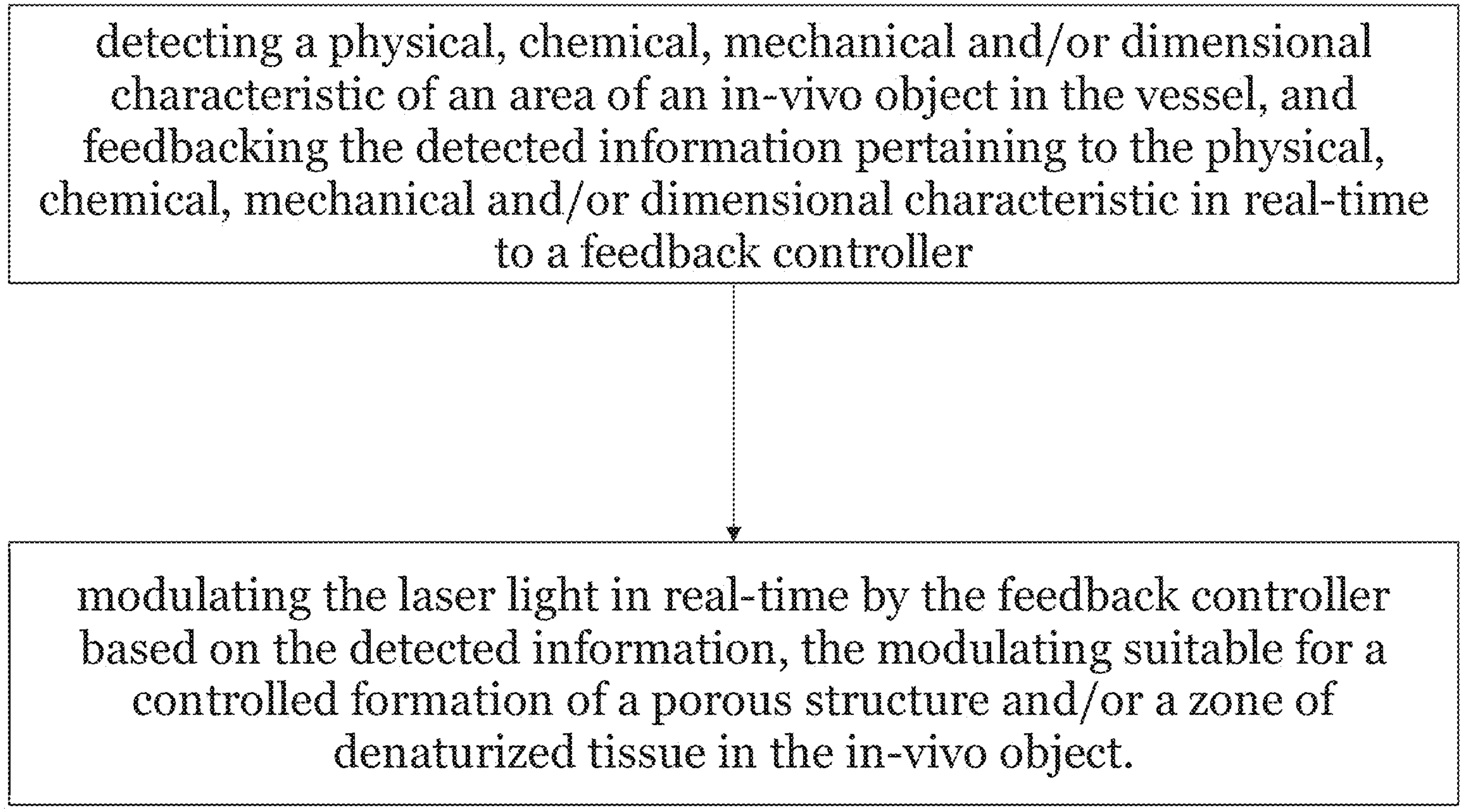
FIG. 6 is a flow chart illustrating a method for treating a calcified blood vessel using a temporal and/or spatial modulated laser light according to an embodiment.

FIG. 6 is a flow chart illustrating a method for treating a calcified blood vessel using a temporally and/or spatially modulated laser radiation according to an embodiment. In this embodiment, the method comprises: a treatment step, wherein the treatment step comprises:

a) detecting a physical, chemical, mechanical and/or dimensional characteristic of an area of an in-vivo object in the vessel, and feedbacking the detected information pertaining to the physical, chemical, mechanical and/or dimensional characteristic in real-time to a feedback controller; and b) modulating the laser light in real-time by the feedback controller based on the detected information, the modulating suitable for a controlled formation of a porous structure and/or a zone of denaturized tissue in the in-vivo object.

In a typical implementation of the method FIG. 6, the method may comprise:

i) a first step of diagnosing the vessel and initiating a working condition of the laser;

ii) a second step of treating a calcified plaque in the vessel; and iii) a third step of treating a vessel wall after the second step is concluded, wherein at least one of the second or third step may comprise the treatment step.

In particular, the second step may comprise softening and molding of the calcified plaque step, a cold lithotripsy step and a laser induced stress relaxation step on the calcified plaque. The third step may comprise a laser induced stress relaxation step on the vessel wall. All three steps may comprise a method of FIG. 5. In the following, the molding, cold lithotripsy, and a laser induced stress relaxation carried out on a calcified plaque and on the vessel wall will be elaborated in detail.

Softening and Molding of Calcified Plaque

In an embodiment, an in-vivo object is a calcified plaque of uneven thickness. The disclosure makes it possible to increase the lumen and compliance of the vessel by molding, i.e., smoothing, of the calcified plaque without destroying it. The molding process includes two steps: (i) the softening of the calcified plaque, which implies decreasing its tensile strength and yield strength through the formation of micro-structural defects, including micropores; and (ii) changing the shape and smoothening the calcified plaque via the application of the mechanical force.

In an exemplary embodiment, this mechanical effect can be realized through a balloon or a stent or by thermomechanical action of the spatially modulated laser radiation. In particular, the applied pressure on a balloon may be 5-12 atm which is lower than the mechanical strength of the vessel wall (15-20 atm) and is much less than the pressure 40-50 atm applied when using most of the conventional methods including the FDA approved shock wave lithotripsy. This ensures the safety of the molding technique since it does not lead to tearing or rupture of the vessel walls.

Cold Lithotripsy

In an embodiment, an in-vivo object is a thick and well-developed calcified plaque, for example a calcified plaque in the case of a CTO. In such case, the molding or softening of the calcified plaque may not occur because an applied power may appear not sufficient enough for expanding a lumen area and normalizing a blood flow in a blood vessel. Yet, the traditional destruction of the calcified plaques using conventional lithotripsy, which requires high temperatures and pressures more than 40 atm, can lead to tearing or rupture of the vessel wall. A CTO is present in nearly 50% of all patients undergoing endovascular treatment of the infrainguinal peripheral arteries where the treatment is especially challenging. In these cases, the present disclosure can be used for a partial destruction of the calcified plaque which allows for the safe solution of the curing problem.

Figure 7A:
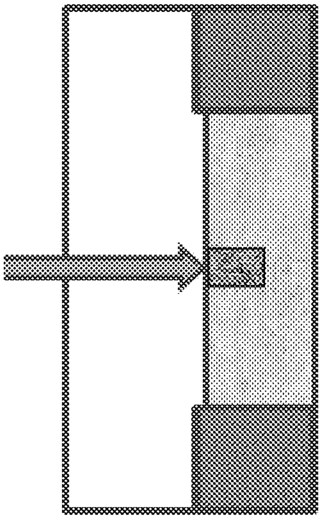
FIG. 7A is a schematic illustration of a method for destroying a calcified plaque (cold lithotripsy) according to an embodiment.

FIG. 7A presents a schematic illustration of a method for destroying a calcified plaque according to an embodiment. In this embodiment, an area of a porous structure is formed on the calcified plaque due to a porous structure formation of the hydroxyapatite in the calcified plaque. The porous structure may have a depth of $$d = \frac{1}{k},$$

where $k=W_0a$ is an effective absorption coefficient, a is the water absorption coefficient, $W_0$ is the initial porosity of a calcified plaque, W is the porosity of the porous structure of the area of the calcified plaque after an initial porous structure formation. The in-vivo object may contain different materials and may have different physical properties. For example, when the laser is a Tm laser; for the Calcium Oxalate, $W_0=9\%$ and $$k = 14\frac{1}{\text{cm}};$$

for Uric Acid $W_0=12\%$, $$k = 19\frac{1}{\text{cm}}.$$

The porosity of a Bego stone can vary depending on the preparation conditions. The threshold for an energy density of the laser ablation (F) of the in-vivo object with the Tm laser may be 20.8 J/cm$^2$ for Calcium Oxalate and 7 J/cm$^2$ for Uric Acid. This may give a temperature increase of ΔT=Fk/c=70° C. for the Ca Oxalate, and 40° C. for the Uric Acid in the porous structure.

$$c = 4.2\frac{\text{J}}{\text{cm}^3}$$

is a heat capacity.

Figure 7B:
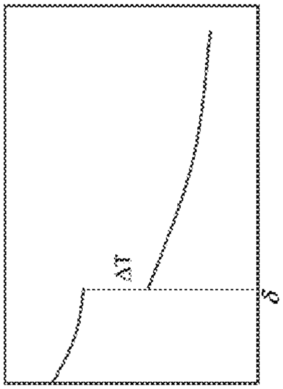
FIG. 7B is a graph illustrating the spatial change of the temperature during a method for destroying a calcified plaque in an example.

A thermo-stress due to water expansion is $$\sigma = \left(\frac{2}{3}\right)G(\beta_a - \beta_0)T = 12 \text{ MPa} \tag{23}$$

for Calcium Oxalate and σ=8 MPa for Uric Acid. Here G=2 GPa is the shear modulus, $$\beta_a - \beta_0 = 10^{-4}\frac{1}{\text{K}}$$

is the thermo-expansion coefficient. The tensile strength is σ=3-5 MPa for Ca Oxalate, σ=2-4 MPa for Uric Acid, σ=3-16 MPa for the Bego stones. After the laser-induced porous structure formation, the porosity in the porous structure may increase by factor of two or three. When the porous structure is filled with water, the thermo-mechanical stress between this area and the rest of the calcified plaque may lead to a removal of the porous structure. FIG. 7*b* shows the temperature gradient between the illuminated porous structure and the surrounding area of the in-vivo object. The boundary between the area of an enhanced water concentration and the surrounding area is denoted as δ.

To calculate the ablation rate in this scenario, one may first consider the time necessary for water to fill the porous structure. For a porous structure of the thickness d, the filling time is $$t_W = \frac{4L^2}{D},$$

where $$D \simeq 10^{-3}\frac{\text{cm}^2}{\text{s}}$$

is the water diffusion coefficient in the porous structure, L is the spatial scale of a porous structure. For example, assuming the modulated laser light is delivered via a round optic fiber with a cross section of a radius R. The ablation rate is $$A = \frac{g\pi R^2 d}{t_W} = \frac{g\pi R^2 dD}{4L^2}$$

where g is a density of the calcified plaque. The value of A increases with D which grows with the temperature and the average power density. If $$R > d = \frac{1}{k},$$

where k=$W_0\alpha$ is the effective absorption coefficient, α is a water absorption coefficient, $W_0$ is an initial porosity of the calcified plaque, W is a porosity of the porous structure after the porous structure formation, the filling time $$t_W = \frac{d^2}{D},$$

then the ablation rate $$A = \frac{g\pi R^2 d}{t_W} = g\pi R^2 Dk.$$

The value of A increases with the growth of the fiber diameter and with the increase of the light absorption coefficient. For R=300 mm, A≅120 mg/s, for a Tm laser, and A≅30 mg/s, for a Ho laser. If d>R, $$t_w = \frac{4R^2}{D},$$

and the ablation rate A=gp D/4 k does not depend on the fiber radius and decreases with the light absorption coefficient. For R=100 mm, A≅90 mg/s for a Tm laser, and A≅360 mg/s for a Ho laser. For the treatment of the calcified plaque with the Erbium glass fiber laser:

$$a = 10\frac{1}{\text{cm}},$$

Figure 7C:
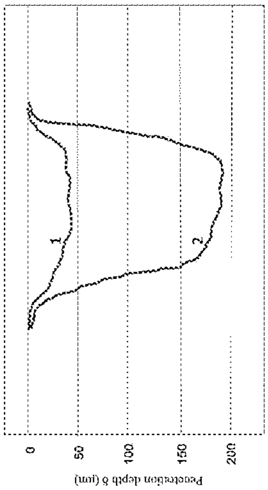
FIG. 7C is a graph illustrating the profile change of a calcified plaque surface during a method for destroying a calcified plaque in an example.

$W_0$=0.3, and A≅500 mg/s. FIG. 7*c* shows profiles of the crater area in the Bego stone treated by the laser system according to the present disclosure. Laser wavelength 1.44 mm, penetration depth d=200 mm, power 10 W, fiber diameter 150 mm, pulse duration 1 ms, number of pulses 100, pulse repetition rate ƒ=80 Hz (for the upper curve), and 4 Hz, for a lower curve.

A significant volume reduction is observed for the lower pulse repetition rate when a time interval between two laser pulses was longer than a time it takes for the water to fill the porous structure.

In a sub-optimal implementation, a pulsed laser may be run with a shorter pulse duration, high pulse repetition rate and high peak power. The short pulse duration and high peak power lead to a dramatic increase of the ablation temperature resulting in the intensive water evaporation. The efficiency may reduce if the pulse repetition rate is too high for the water to fill the porous structure. In this embodiment, the laser radiation may be temporally modulated to magnify the above-mentioned effect. For example, the time period between two pulses (inverse of the repetition rate of the pulsed laser) may be optimized to increase a laser efficiency. In particular, a time period between two pulses should be long enough for the water to fill the porous structure, but short enough for a continuous generation of temperature gradient.

Thus, the present disclosure provides an effective method to treat severe calcified blood vessel including the calcified blood vessel in CTO.

Laser Induced Stress Relaxation

The present disclosure can be used to reduce a mechanical stress on the calcified plaque or on the vessel wall without destroying their structures on a macroscopic level.

The mechanical stress of an in-vivo object in a blood vessel is one of the origins of the poor elasticity and low compliance of the blood vessel. Therefore, a stress relaxation is one of the effective methods of the blood vessel treatment. The stress relaxation occurs when some elements within an area of the in-vivo object acquire an ability to move with respect to another elements, and the elastic energy dissipates or transforms to other types of energy like thermal energy, phase transformation, surface energy, etc. For example, stress relaxation can be achieved due to porous structure formation when stress energy transforms into a surface energy of pores due to the formation of the porous structure.

Figure 8C:
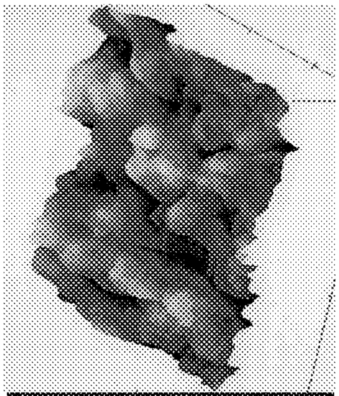
FIG. 8C is an AFM image illustrating of a den arisen in the vessel wall between normal collagen fibers in an example.

In biological tissues, for example, vessel walls, the secondary and tertiary structures of proteins and nucleic acids contain, as basic elements of their structure composure, the intermolecular hydrogen bonds. With an increase in temperature and in the presence of the mechanical stresses, breaking of the intermolecular bonds may lead to a movement of some elements of the structure with respect to others. This relative movement diminishes the general energy of the system and leads to a relaxation of the stress. In the zones of the broken intermolecular bonds, structural defects appear, in particular, zones of the denatured tissue and porous structure, for example a microporous structure, where pores are filled with gases dissolved in the tissue fluid, mostly carbon dioxide, oxygen, and nitrogen. In this case, two types of defects are formed: dens, which are the zones of the denaturized tissue, and micropores filled with the gas bubbles, often referred to as nano bubbles. Increasing the pressure diminishes the gas solubility, and the gas transforms into its solved state, the large bubbles collapse, and the number of dens increases. FIG. 8*c* shows an AFM image illustrating a den arisen in the vessel wall between normal collagen fibers in an example.

On a macroscopic scale, the laser-induced breaking of the intermolecular bonds in an in-vivo object can lead to a denaturization, i.e., the violation of the ordered protein structure, of tissues and formation of a porous structure or other defects between the zones with the unchanged structures. The interaction of dens and bubbles can inhibit the processes of denaturation, plastic deformation, or the formation porous structure. Porous structure or other defects can play a versatile role in processes in a blood vessel. In particular, the porous structure can reduce the mechanical strength of calcified plaques and can enhance the delivery of drugs to the vessel walls through a calcified plaque. That facilitates a healing of the blood vessel, preventing recalcification and restenosis. On the other hand, an uncontrolled growth of the dens and porous structure may lead to development of the processes of denaturation and tearing in the vessel wall, which can be harmful for their mechanical properties.

Figure 8B:
FIG. 8B is a SIM image illustrating $Ca^{+2}$ ions covering the surface of a gas bubble in an artery plaque in an example.
Figure 8A:
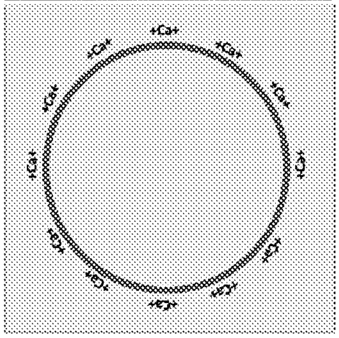
FIG. 8A is a schematic illustration of a mechanism of a stabilized gas bubble for stabilizing a microporous structure according to an embodiment.

FIG. 8A shows a stabilized gas bubble covered with $Ca^{2+}$ ions, FIG. 8*b* shows a SIM image illustrating $Ca^{2+}$ ions covering the surface of a $CO_2$ gas bubble in an artery plaque.

Figure 9:
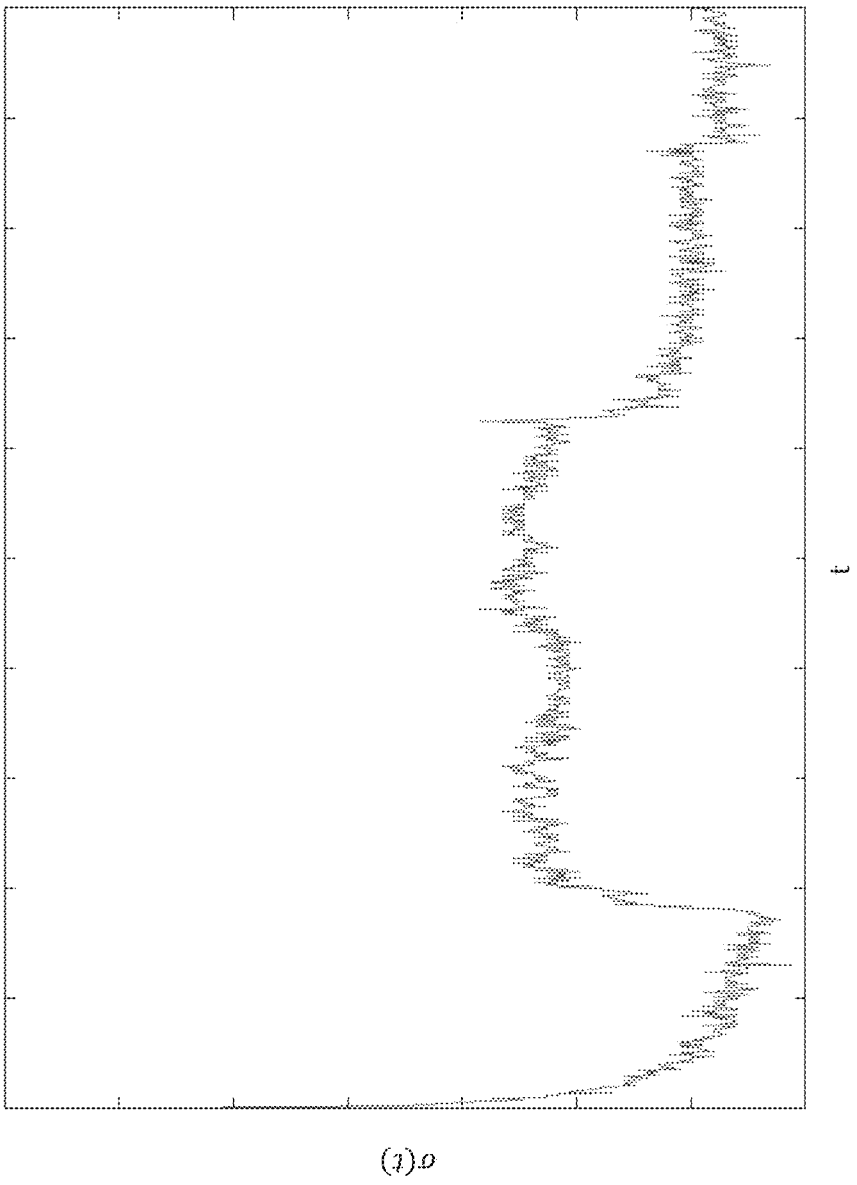
FIG. 9 is a graph illustrating the time dependency of a conductivity of a vessel wall under a continuous laser illumination in an example.

The porous structure can be either temporary or stabilized, hence long-living. The porous structure, in particular microporous structure, can be stabilized by gas bubbles, for example nanobubbles and their agglomerates, the surface of which is covered with the positive ions such as calcium ions. Gas bubbles arise in liquids in which gases are dissolved with a solubility dependent of temperature. Gas bubbles arising and growing during the heating in liquids are usually unstable and collapse rapidly. The presence of the calcium ions in tissue fluids can stabilize the bubbles. The ions located at the surface of the gas bubbles repel each other, which prevents the bubble from collapsing. Further, the ions at the surface of the bubbles slow down the bubbles' movement. The features associated with the formation of the stable bubbles and their destabilization, which occurs at a certain temperature, manifests in the dependence of the electric current upon temperature. FIG. 9 demonstrates the time dependency of the electric conductivity $\sigma(t)$ of the calcified artery of the cadaver. In this example, a detecting element comprises a conductivity detecting element, which comprises electrodes in the form of the two coaxial cylinders truncated at an acute angle of about 20 degrees. A first electrode is a quartz light guide with a diameter of 600 μm, covered with an aluminum sheath. The proximal end of the light guide is glued with conductive glue and then covered with a thin layer of electrically insulating acrylic varnish. The distal end of the fiber, at a length of 3 mm, is de-coated. A cylindrical metal tip is put on this end. In the beginning of the laser irradiation, the electrical conductivity increases due to temperature increase. After about 3 s of the irradiation, the electrical conductivity decreases due to formation of gas bubbles. After about 7 s of irradiation these bubbles disappear due to heating up to the temperatures above 60-70° C. and an escape of the stabilizing ions.

Figure 10:
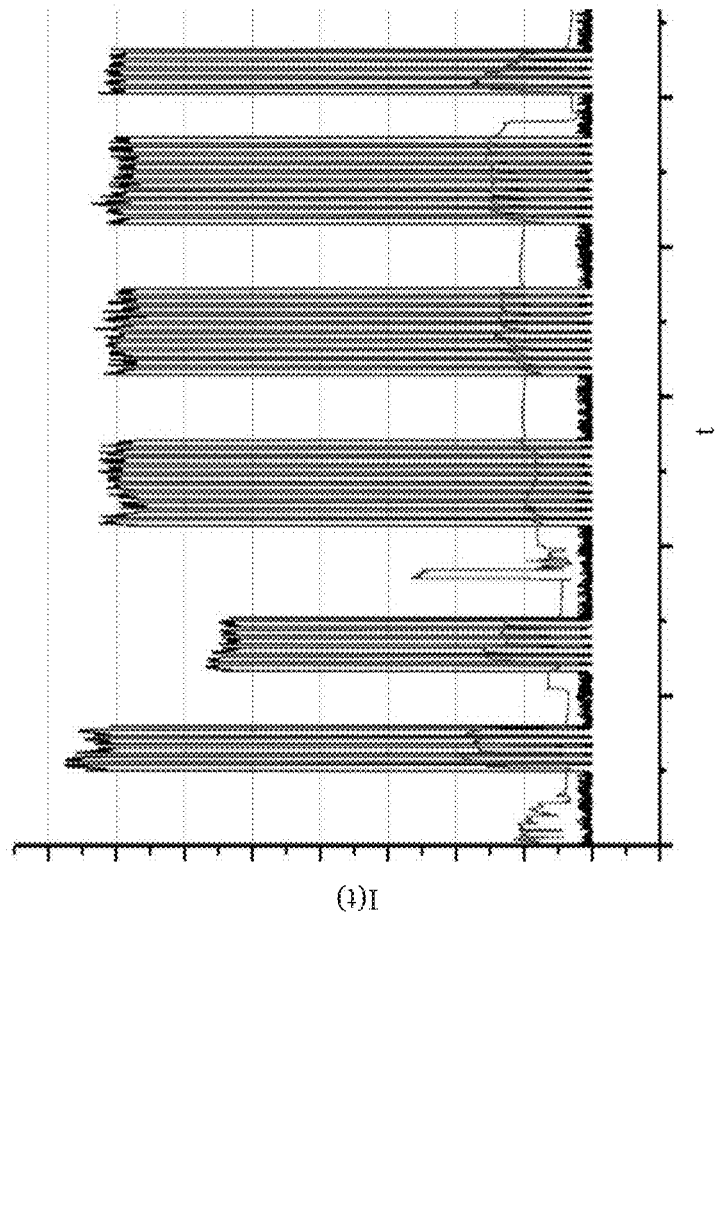
FIG. 10 is a graph illustrating the time dependencies of the laser intensity and an intensity of feedback signal in an example.

Light scattering is also very sensitive to the formation of porous structure or zones of the denaturized tissues. Measurements of the scattering of light of different wavelengths make it possible, using the Mie and Rayleigh scattering laws, to determine the prevailing defect size. Measuring the time dependencies of the light scattering makes it possible to study the stability of the gas bubbles, porous structure, or zones of the denaturized tissues and to establish the boundaries of the treatment working conditions for the laser. The controller may process the detected light scattering and modulate the laser during laser treatment. For example, the feedback controller stops the irradiation when a preset threshold is achieved by the detected information pertaining to the scattered light. FIG. 10 demonstrates time dependencies intensities of the modulated laser (denoted in bars) and the intensity of detected scattered light (denoted in lines) in an example, demonstrating how the laser intensity can be modulated based on the detected information. In this example, a calcified artery of a pig is treated using several series of laser pulses.

The feedback controller decreased the laser power by over 25% after the first series of 8 pulses, and after the second series the power was increased by 20%. Then the three series of 12 pulses each, were applied. Irradiation was terminated during the sixth series, when the intensity of the scattered light significantly decreased after each subsequent pulse. This reflects a tendency for individual defects (porous structure or zones of denaturized tissues) to grow excessively. The reliability of such a controller is tested using OCT and histology.

Stress relaxation of the calcified blood vessel may include porous structure formation in an area of hydroxyapatite in the medial and intimal calcification zones.

Elimination of the stress can also occur due to a local denaturation of tissues such as pathological oriented collagen fibers which may be responsible for excessive expansive stress at the boundary between vessel wall and calcified plaque. Near the calcified areas, a pronounced change in the distribution of stresses can be observed from predominantly circumferential to predominantly longitudinal or in thickness. Stress can be relaxed due to local denaturation of abnormal orienteered collagen fibers.

For laser induced stress relaxation, a temperature should be controlled within a certain range. The mechanisms of the laser induced stress relaxation may include: (i) a bound-to-free transition of tissue water, (ii) a reorganization of the collagen structure at the boundary zone between vessel walls and calcified plaques including local denaturation and breaking the abnormal collagen fibers and crosslinks. (iii) formation and movement of structural defects (including zones of denaturized tissues and porous structures) resulting in the reduced energy in the in-vivo object. All the above processes require heating to temperatures of 45-70° C. for a time interval shorter than a time interval required for denaturation of large zones (larger than fifty microns).

Thus, the laser system according to the present disclosure makes it possible to control the laser-induced porous structure formation and laser-induced formation of zones of the denaturized tissues, and to provide the safety of the laser treatment.

Treating of Residue Stress on a Vessel Wall

In another embodiment, the laser system is used in a third step of treating a vessel wall after the second step is concluded. The third step may also be carried out after other cardio intervention including molding, a traditional lithotripsy, or stenting of the blood vessel.

In an embodiment, the in-vivo object is calcified plaque or a vessel wall with residue stress. Residue stresses can arise after plastic deformation processes, which occur, for example, during the molding or lithotripsy in the second step of treating a calcified plaque in the vessel.

For example, the porous structure formation and stress relaxation of the calcified plaques are accompanied by plastic deformation which, after seeded external force, leads to the formation of the residue stress. Residue stresses after the plastic deformation are also inevitable after a stenting surgery. Residue stress amplitude can be calculated using the model of plastic deformation in calcified vessels and measured using an OCE method. Removal of the residue stress may be a final step for a laser treatment of the calcified blood vessel according to the present disclosure. In an example, this procedure can be performed using irradiation of a laser with a wavelength of 1060 nm, a pulse duration of 1 ms, a power of 2 W, a pulse repetition rate of 10 Hz, wherein the laser signal comprises three series of laser pulses of 10 pulses each with a period between series of 10 s.

Figure 11:
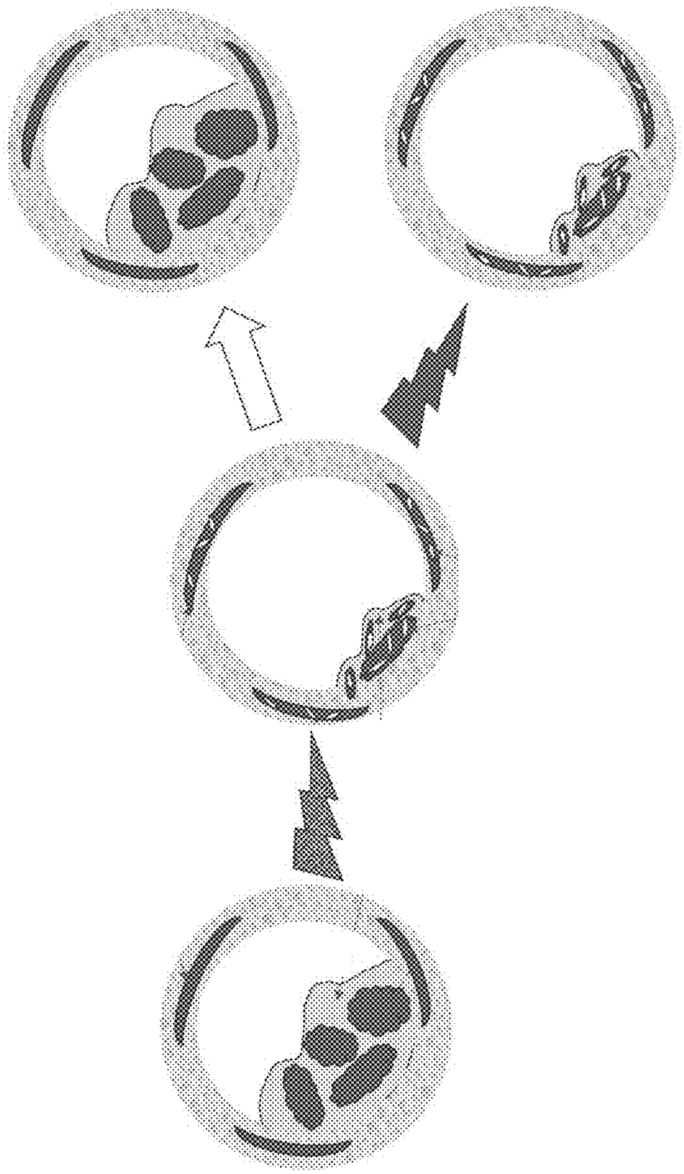
FIG. 11 is a schematic illustration of a method for reducing a residue stress on a vessel wall according to an embodiment.

Eliminating a residue stress on a vessel wall or a calcified plaque layer attached to the vessel wall is an important procedure which diminishes secondary effects and the long-term biological response of the blood vessel after any physical treatment accompanied by plastic deformation. In addition, the formation of a porous structure enhances the diffusion of the drug to the vessel walls and also prevents recalcification, calcinosis and restenosis in the blood vessel. As shown in FIG. 11, after a second step of treating the calcified plaque in the blood vessel, a volume of the calcified plaque can be reduced, and a lumen area can be expanded (the status of the blood vessel changes from the states denoted on the left of FIG. 11 to the status denoted in the middle of FIG. 11). The blood vessel wall and the calcified plaque attached to the blood vessel wall may be then treated through a laser induced stress relaxation step, which leads to a long-term stability (the status denoted on the bottom right of FIG. 11). Without such stress relaxation, recalcification may occur several months after the treatment (the status denoted on the upper right of FIG. 11).

A functional stiffness of the vessels is governed by their material stiffness and geometry characterized by the vessel lumen area, the vessel radius r, and the thickness of the vessel walls h, which is a combination of the morphology and disease. An increase in a smooth muscle tone in the muscular arteries that represents most of the conduit vessels alters the pressure-to-volume relationship in these vessels and results in a decrease in an arterial compliance or elasticity. The laser-induced stress relaxation allows to decrease the smooth muscle tone in the arteries and to increase their compliance. The laser-induced reduction of the residue stress in the vessel walls also decreases the rate of the recalcification processes, disrupts or reverses processes of formation of the calcified plaques.

Mathematical Model for the Real-Time Laser Modulation

In the following, the mathematical model of the laser-induced formation of a porous structure and a zone of denaturized tissue based on the thermal, thermo-mechanical and mechanical equations considering the laser induced intermolecular bond breaking in the calcified plaque is elaborated. With the mathematical model, the skilled person in the art may find no difficulties in realizing and optimizing a real-time modulation of the laser for a controlled formation of porous structure and a zone of denaturized tissue based on the real-time detected information, for example, through an encompassing the mathematical model into a feedback algorithm.

The processes occurring in a continuous medium under a laser radiation can be described by the equations of motion of the medium in the form of Lagrange equations which describe the motion of multilayer media, the properties of which change when passing through the interfaces. Consider the Lagrange equations for a three-dimensional motion of a continuous medium. The continuity equation in Lagrange variables has the form:

$$V=V_0\Delta \quad (1)$$

where $$\Delta = \frac{\partial(x_e, y_e, z_e)}{\partial(x_1, y_1, z_1)}$$

is the Jacobean for the transition from the Euler coordinates $(x_e,y_e,z_e)$ to Lagrange coordinates $(x_1,y_1,z_1)$;

$$V_0 = \frac{1}{\rho_0}$$

is an initial specific volume, $$V = \frac{1}{\rho}$$

is a current specific volume. In an explicit form, the continuity equation can be written as follows $$V = V_0\left[\frac{\partial x_e}{\partial x_1}\left(\frac{\partial y_e}{\partial y_1}\frac{\partial z_e}{\partial z_1} - \frac{\partial y_e}{\partial z_1}\frac{\partial z_e}{\partial y_1}\right) - \quad (2)\right.$$

-continued $$\frac{\partial y_e}{\partial x_1}\left(\frac{\partial x_e}{\partial y_1}\frac{\partial z_e}{\partial z_1}-\frac{\partial x_e}{\partial z_1}\frac{\partial z_e}{\partial z_1}\right)+\frac{\partial z_e}{\partial x_1}\left(\frac{\partial x_e}{\partial y_1}\frac{\partial y_e}{\partial z_1}-\frac{\partial x_e}{\partial z_1}\frac{\partial y_e}{\partial y_1}\right)\Bigg]$$

The equations of motion in the Lagrange form are then $$\left(X-\frac{\partial^2 x_e}{\partial t^2}\right)\frac{\partial x_e}{\partial x_1}+\left(Y-\frac{\partial^2 y_e}{\partial t^2}\right)\frac{\partial y_e}{\partial x_1}+\left(Z-\frac{\partial^2 z_e}{\partial t^2}\right)\frac{\partial z_e}{\partial x_1}=\frac{1}{\rho}\frac{\partial P}{\partial x_1}; \quad (3)$$

$$\left(X-\frac{\partial^2 x_e}{\partial t^2}\right)\frac{\partial x_e}{\partial y_1}+\left(Y-\frac{\partial^2 y_e}{\partial t^2}\right)\frac{\partial y_e}{\partial y_1}+\left(Z-\frac{\partial^2 z_e}{\partial t^2}\right)\frac{\partial z_e}{\partial y_1}=\frac{1}{\rho}\frac{\partial P}{\partial y_1}; \quad (4)$$

$$\left(X-\frac{\partial^2 x_e}{\partial t^2}\right)\frac{\partial x_e}{\partial z_1}+\left(Y-\frac{\partial^2 y_e}{\partial t^2}\right)\frac{\partial y_e}{\partial z_1}+\left(Z-\frac{\partial^2 z_e}{\partial t^2}\right)\frac{\partial z_e}{\partial z_1}=\frac{1}{\rho}\frac{\partial P}{\partial z_1}, \quad (5)$$

where $\vec{F}=X\vec{i}+Y\vec{j}+Z\vec{k}$ is a force vector per unit mass, which hereafter can be assumed to be equal to zero, namely X=Y=Z=0.

Considering the explicit form of the equations for changing the Euler coordinates $$u_{x_e}=\frac{\partial x_e}{\partial t},\ u_{y_e}=\frac{\partial y_e}{\partial t},\ u_{z_e}=\frac{\partial z_e}{\partial t}, \quad (6)$$

The system (3)-(5) acquires the form $$\frac{\partial u_{x_e}}{\partial t}\frac{\partial x_e}{\partial x_1}+\frac{\partial u_{y_e}}{\partial t}\frac{\partial y_e}{\partial x_1}+\frac{\partial u_{z_e}}{\partial t}\frac{\partial z_e}{\partial x_1}=-\frac{1}{\rho}\frac{\partial P}{\partial x_1}, \quad (7)$$

$$\frac{\partial u_{x_e}}{\partial t}\frac{\partial x_e}{\partial y_1}+\frac{\partial u_{y_e}}{\partial t}\frac{\partial y_e}{\partial y_1}+\frac{\partial u_{z_e}}{\partial t}\frac{\partial z_e}{\partial y_1}=-\frac{1}{\rho}\frac{\partial P}{\partial y_1}, \quad (8)$$

$$\frac{\partial u_{x_e}}{\partial t}\frac{\partial x_e}{\partial z_1}+\frac{\partial u_{y_e}}{\partial t}\frac{\partial y_e}{\partial z_1}+\frac{\partial u_{z_e}}{\partial t}\frac{\partial z_e}{\partial z_1}=-\frac{1}{\rho}\frac{\partial P}{\partial z_1}, \quad (9)$$

Resolving equations (7)-(9) with respect to $$\frac{\partial u_i}{\partial t}$$

and considering the explicit form of the continuity equation (2), leads to the following system of equations of motion $$\frac{\partial u_{x_e}}{\partial t}=-V_0\left[\frac{\partial P}{\partial x_1}\left(\frac{\partial y_e}{\partial y_1}\frac{\partial z_e}{\partial z_1}-\frac{\partial y_e}{\partial z_1}\frac{\partial z_e}{\partial y_1}\right)-\frac{\partial y_e}{\partial x_1}\left(\frac{\partial P}{\partial y_1}\frac{\partial z_e}{\partial z_1}-\frac{\partial P}{\partial z_1}\frac{\partial z_e}{\partial y_1}\right)+\frac{\partial z_e}{\partial x_1}\left(\frac{\partial P}{\partial y_1}\frac{\partial y_e}{\partial z_1}-\frac{\partial P}{\partial z_1}\frac{\partial y_e}{\partial y_1}\right)\right], \quad (10)$$

$$\frac{\partial u_{y_e}}{\partial t}=-V_0\left[\frac{\partial x_e}{\partial x_1}\left(\frac{\partial P}{\partial y_1}\frac{\partial z_e}{\partial z_1}-\frac{\partial P}{\partial z_1}\frac{\partial z_e}{\partial y_1}\right)-\frac{\partial P}{\partial x_1}\left(\frac{\partial x_e}{\partial y_1}\frac{\partial z_e}{\partial z_1}-\frac{\partial x_e}{\partial z_1}\frac{\partial z_e}{\partial y_1}\right)+\frac{\partial z_e}{\partial x_1}\left(\frac{\partial x_e}{\partial y_1}\frac{\partial P}{\partial z_1}-\frac{\partial x_e}{\partial z_1}\frac{\partial P}{\partial y_1}\right)\right], \quad (11)$$

$$\frac{\partial u_{z_e}}{\partial t}=-V_0\left[\frac{\partial x_e}{\partial x_1}\left(\frac{\partial y_e}{\partial y_1}\frac{\partial P}{\partial z_1}-\frac{\partial y_e}{\partial z_1}\frac{\partial P}{\partial y_1}\right)-\frac{\partial y_e}{\partial x_1}\left(\frac{\partial x_e}{\partial y_1}\frac{\partial P}{\partial z_1}-\frac{\partial x_e}{\partial z_1}\frac{\partial P}{\partial y_1}\right)+\frac{\partial P}{\partial x_1}\left(\frac{\partial x_e}{\partial y_1}\frac{\partial y_e}{\partial z_1}-\frac{\partial x_e}{\partial z_1}\frac{\partial y_e}{\partial y_1}\right)\right], \quad (12)$$

The Mie-Grüneisen equation in its two-term form to approximate the equation of state may be written as $$P=P_X+P_T=\rho_0 u_0^2\left(1-\frac{V}{V_0}\right)+\Gamma\frac{c_V(T-T_0)}{V}, \quad (13)$$

where $P_T$ and $P_X$ are the thermal and cold components of pressure P, $$\Gamma=\frac{u_0^2\beta}{c_V}$$

is the Grüneisen coefficient, β is the coefficient of volumetric expansion, $c_V$ is the heat capacity, and $u_0$ is the speed of sound in the medium.

The change in the temperature of the medium can be found from solving the heat conduction equation:

$$\rho c_V\frac{\partial T}{\partial t}=k_T\left(\frac{\partial^2 T}{\partial x_e^2}+\frac{\partial^2 T}{\partial y_e^2}+\frac{\partial^2 T}{\partial z_e^2}\right)+Q_S \quad (14)$$

The value of $Q_S$ in equation (14) is determined by the source of energy release: $Q_S=I(x_e,y_e,z_e,t)\kappa$, where $I(t,x_e,y_e,z_e)=I_0 f_t(t) f_{xyz}(x_e,y_e,z_e)$ is the intensity of the light beam at the moment t at the point in space with the coordinate $(x_e,y_e,z_e)$, κ is the absorption coefficient of the medium.

A pulse periodic function $f=f_t(t)$ may take one or a combination of, but not restricted to the following forms:

(a) sin(ωt), (b) a step function: during the pulse $f=1$, and during time between pulses $f=0$ or $$f_t(t)=\frac{t}{\tau_p}\exp\left[-\frac{t}{\tau_p}\right],$$

where $\tau_p$ is pulse duration.

(c) several series of laser pulses with some delay between series.

The solution of the system (1)-(14) makes it possible to calculate spatial-temporal dependencies of the pressure, temperature, density, and velocity, to evaluate the contribution of thermal and acoustic mechanisms to the change in the physical parameters of a continuous medium.

To determine the distribution function of the intensity of a Gaussian light beam in a simultaneously absorbing and scattering medium, the following law of light beam attenuation can be used, considering the change in its amplitude and spatial shape.

$$I(x_e,y_e,z_e)=I_0\exp\left[-\frac{y_e^2+z_e^2}{r_0^2(x)}\right]\exp\left[-(k_{abs}+k_{scat})x\right], \quad (15)$$

where $k_{abs}$ and $k_{scat}$ are absorption and scattering coefficients, respectively. The radius of the light beam changes as it penetrates the medium according to the law:

$$r_0^2(x)=r_0^2(x=0)\exp[k_{scat}x],$$

expanding exponentially due to scattering and maintaining a Gaussian shape in cross section. Using equation (15), the energy release function in equation (14) acquires the form:

$$Q_S(t, x_e, y_e, z_e) = I_0\left(\frac{t}{\tau_p}\right)\exp\left[-\frac{t}{\tau_p}\right]\exp\left[-\frac{y_e^2+z_e^2}{r_0^2(x)}\right]\exp\left[-(k_{abs}+k_{scat})x\right] \quad (16)$$

As a result, the 3D fields of thermal stresses and strains developing in the biological tissues under the effect of pulse-periodic laser radiation with a wide range of laser parameters, including laser wavelength, pulse duration, pulse repetition rate, spatial distribution of power density is obtained. In this way, the parameter defining a working condition of the modulated laser can be adjusted to achieve a desired effect on the illuminated area based on the detected information pertaining to the temperature and the mechanical stress.

In addition, a second mathematical model can be considered. As outlined above, a laser induced stress relaxation of the in-vivo object is due to the formation of porous structures and zones of denaturized tissues. The porous structures and zones of denaturized tissues are formed due to laser induced breaking of intermolecular bonds. In more detail, the mechanism of the laser-induced stress relaxation can be seen as stemming from a non-uniform distribution of the structure and mechanical properties in the area, comprising relatively strong domains separated by less strong interlayers, the destruction of which gives mobility to one domain of the area relative to another domain. Laser heating leads to the breaking of hydrogen intermolecular bonds. Breaking energy of the intermolecular bonds depends on external stresses. Therefore, in a deformed region, the intermolecular bonds are broken more intensively. Regions with the reduced binding energy will deform more. The inhomogeneity of the structure and mechanical properties of the in-vivo object may increase during heating induced by laser illumination, which may lead to the inhomogeneity of deformation to appear in areas where the deformation is large at low loads.

Solving a variational problem of minimizing an elastic energy by changing the structure, redistributing the shape and position of the elements of the system, becomes possible with the model describing a process of thermally activated breaking of the chemical bonds. The latter process determines the kinetics of stress relaxation in the system. In this case, the porous structure formation process depends essentially on only the characteristic bond-breaking energy in the Arrhenius formula for the probability of the bond-breaking, but the value of this parameter can be different at different locations and at different times. It is a given function of temperature, temperature gradient, and the spatial distribution of the binding energy.

Changing the density of intermolecular bonds may comprise two processes occurring simultaneously: a process of reducing the density of intermolecular bonds, and a process of deformation due to the tendency of a substance in the in-vivo object to minimize its internal energy. The potential barrier for the intermolecular bond breaking is high enough, and the probability of the intermolecular bond breaking per unit time is defined by the Arrhenius law $$p = p_0 e^{-\frac{U}{kT}} \quad (17)$$

where $p_0$ is the preexponential factor, U is the height of the barrier, and T is the temperature. If the tissue is heated, for example due to radiation induced by a laser, above a normal temperature for a short time, the rate of the thermal destruction of the intermolecular bonds given by equation (17) may increase, and during the heating period a considerable part of the intermolecular bonds may be broken. As a result, the stiffness of the area decreases. If the tissue is deformed by the external forces and constraints, or if it has internal stresses, then the height U of the potential barrier may decrease.

The exemplary, but not necessarily the only possible, description is based on an assumption that all the elastic properties of the tissue near the point x depend on one parameter a(x) which may be referred to as an "intermolecular bond density". The value a=1 corresponds to an intact tissue with its maximal strength, while a=0 corresponds to a tissue with completely destroyed structure, effectively without any strength, so that the shear modulus is equal to zero. All the non-homogeneity of the tissue is described by the variations of the parameter a depending on the location; a=a(x).

The tissue in a free state, i.e., free of the external forces, may occupy a 3-dimensional domain $M_0$, and its bond density may be given by function a(x), $x \in M_0$. A deformed tissue may occupy another domain $M_1$, and its configuration can be defined by a mapping $x \rightarrow y(x)$ from $M_0$ to $M_1$. Assume that this mapping is a one-to-one mapping and sufficiently smooth, and that the inverse mapping $y \rightarrow x(y)$ is also sufficiently smooth.

The matrix $$T_{ij} = T = \frac{\partial y}{\partial x} = \frac{\partial y_i}{\partial x_j}$$

can be always represented as a product of a pure deformation, i.e., a transformation represented by a symmetric matrix D and a rotation represented by a rotation matrix R:T=RD. This representation is unique. The energy density function ε does not depend on the rotation R, because rotating a deformed body (or its element) does not change its elastic energy. Further, the symmetric matrix D has 3 orthogonal axes of deformation and 3 positive eigenvalues $\lambda_1$, $\lambda_2$, $\lambda_3$, so that it can be transformed with a proper orthogonal basis into a diagonal form with the eigenvalues $\lambda_j$. An assumption based on the local isotropy of the tissue means that the function E depends only on the eigenvalues $$\lambda_j \cdot T_{ij} = \frac{\partial y_i}{\partial x_j},$$

and $\sigma_i$ are the symmetric combinations of the eigenvalues of the deformation matrix D.

The free energy is defined by the integral $$E = \int_{M_0} \varepsilon\left(x, a(x), \frac{\partial y}{\partial x}\right) d^3x, \quad (18)$$

Where: $\varepsilon(x, a, N) = F(x, a, \sigma_1, \sigma_2, \sigma_3)$,

Following the Mooney-Rivlin model used for biological tissues including for cardiovascular stresses:

$$F = \mu\left(\sigma_3 + \frac{1}{\sigma_3} - 2\right) + a\nu\left(\sigma_1^2 - 3\sigma_2\right), \tag{19}$$

$$\sigma_1 = \lambda_1 + \lambda_2 + \lambda_3,\ \sigma_2 = \lambda_1\lambda_2 + \lambda_2\lambda_3 + \lambda_3\lambda_1,\ \sigma_3 = \lambda_1\lambda_2\lambda_3$$

Here μ and ν are the volume and shear modules.

The differential equations describing the equilibrium of the elastic body are the Euler equations of the variational problem which are the following:

$$\sum_j \frac{\partial}{\partial x_j}\varepsilon_{i,j}\left(x, \frac{\partial y}{\partial x}\right) = 0 \tag{20}$$

$$\varepsilon_{i,j} = \frac{\partial \varepsilon}{\partial T_{ij}}(x, a, T) \tag{21}$$

Equations (18)-(20) describe deformations that affect thermomechanical intermolecular bond breaking and the porous structure formation due to the breaking of chemical bonds.

The strain reduces the potential barrier U for the intermolecular bond breaking, so that instead of U the potential barrier becomes U−ΔU. The difference ΔU is proportional to the elastic energy released as a result of the breaking of one intermolecular bond:

$$\Delta U(x) \sim a\frac{\delta E}{\delta a(x)dx} \tag{22}$$

where E is elastic energy, the variational derivative is defined as $$\frac{\delta E}{\delta a(x)dx} = \frac{1}{2}\frac{\partial \varepsilon(x, a(x), T(x))}{\partial a} \tag{23}$$

Where $$\varepsilon = \varepsilon\left(x, a(x), \frac{\partial y(x)}{\partial x}\right)$$

is the energy density for an energy minimizing configuration y(x).

The probability of the intermolecular bond breaking per unit time at the point x and at the time t is given by the Arrhenius law:

$$p = p_0 e^{-\frac{U-\Delta U}{k\theta}}, \tag{24}$$

where $$\Delta U(x) = \alpha\frac{\delta E}{\delta a(x)dx} = \frac{\alpha}{2}\frac{\partial \varepsilon(x, a(x), T(x))}{\partial a}$$

and the equation defining the time evolution of the bond density a(x,t) becomes $$\frac{\partial a}{\partial t} = -(a - a_0)p \tag{25}$$

where p=p(x,t) is defined by the equations (24). The right-hand side of (24), in its turn, is defined by the solution of the variational problem with the function a(x,t) obtained by this moment, and the given boundary conditions and temperature field. Here a is the coefficient of proportionality between the decrease in the activation energy of intermolecular bonds and the variational derivative of the free energy of the tissue. The parameter $a_0$ is the residue intermolecular bond density, representing a strength remaining in the tissue after a long heating (about 5-10%). The entire volume is divided into small elementary volumes (cubes), in which all parameters are considered constant.

Figure 12:
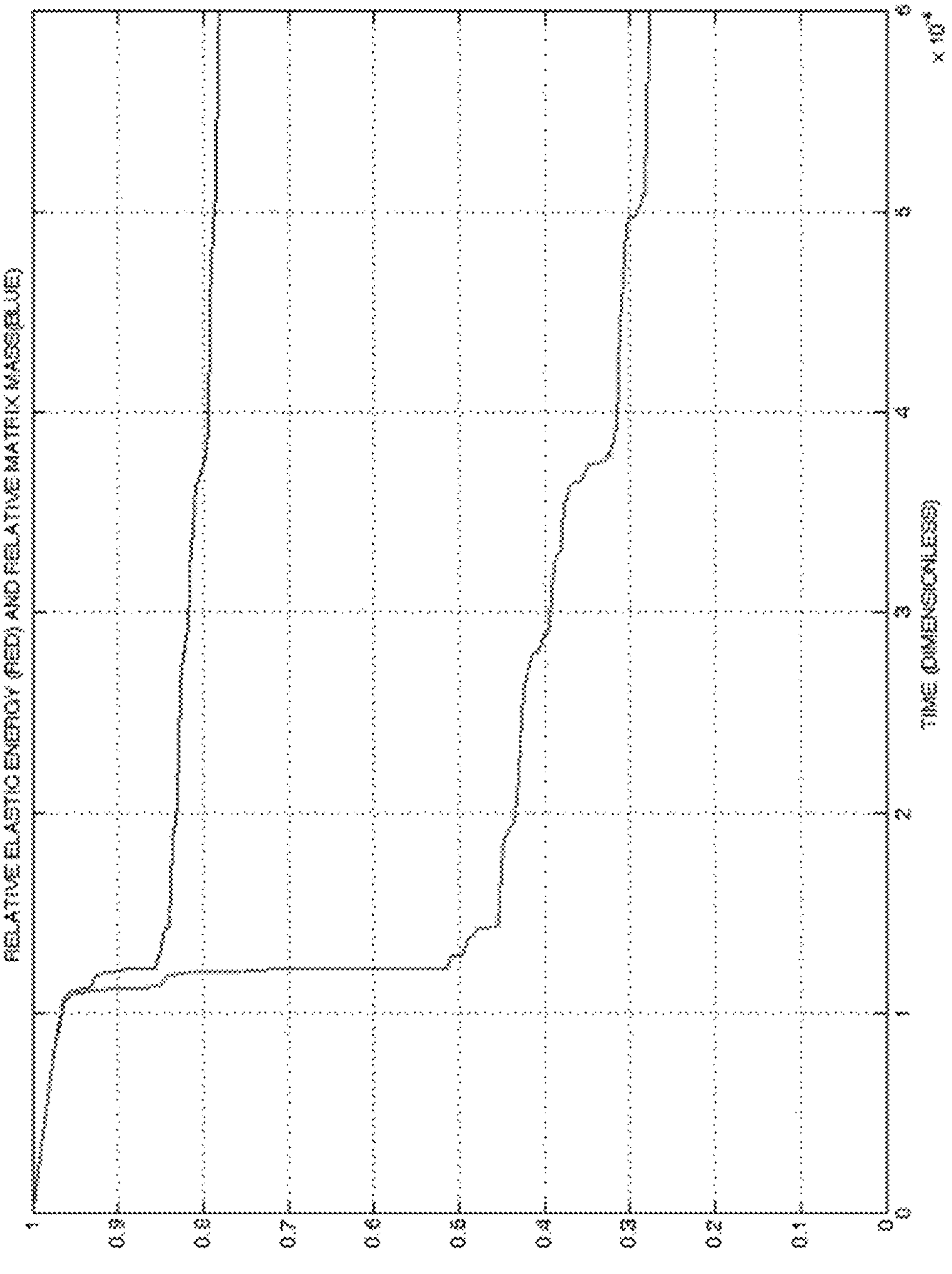
FIG. 12 is a graph illustrating the time dependencies of a relative elastic energy and a relative matrix mass in an example.

Solving the inverse problem of determining the parameters of the laser, including parameters defining the laser working conditions, facilitates increasing the elasticity of the vessels, softening the calcified plaque or the vessel wall, or destruction of the calcified plaque, which minimizes the negative outcomes such as unwanted vessel wall denaturation. FIG. 12 demonstrates results in the changes over time in the total energy of the system and the number of unbroken bonds of an example.

Further, other important conclusions can be drawn from the theoretical model when applying it in an environment corresponding to an atherosclerotic vessel: (1) The deformation is concentrated in certain areas, while a significant part of the in-vivo object practically does not experience deformations. (2) The rupture of intermolecular bonds and stress relaxation occurs in both compressed and stretched areas of the in-vivo object. Therefore, a relaxed stress in this disclosure may refer to both reduced compression and reduced stretching (3) For stress relaxation, it is enough to break only 10-20% of the intermolecular bonds. (4) Three stages of stress relaxation may exist: slow, rapid, and slow again. (5) An abrupt change in the elastic energy is characteristic of the evolution of structural inhomogeneities in non-crystalline polymers in the in-vivo object.

In a disclosed example, the detected information for the information processing is detected using a combination of CT, OCT and US microscopy based on a Sound Amplification by Stimulated Emission of Radiation (SASER) that emits coherent acoustic waves penetrating the blood vessel on the depth of 1 mm and gives precise information about structure and dimensions of the calcified plaque. During the laser treatment, the detected information is processed in real-time by the feedback controller. The feedback controller adjusts the laser parameters during the laser treatment and stops the radiation when a predetermined threshold is achieved.

Examples of Successful Treatments

The present disclosure has been implemented in a couple of preliminary experiments disclosed below. Although the disclosure has been implemented in these examples. These examples may contain extra steps, which should be not seen as restrictive to the present disclosure.

First Example

The atherosclerotic changes in eight iliac arteries of four pigs were modeled by a Diabetic/Hypercholesterolemic (DM/HC) method. Two pigs were sacrificed in 6 months and the remaining two in 9 months after the start of the experiment. The presence and dimensions of the calcified plaques in the artery were established using computer tomography and IVUS. The diameter of the arteries was 3.6+/−0.4 mm, vessel wall thickness was 380+/−10 μm. A development of calcified plaques was demonstrated which are 0.6+/−0.2 and 1.0+/−0.4 mm thick, obtained at 6 and 9 months after DM/HC induction, respectively.

Mechanical properties, including the Young's module and stress in the zone at the boundary between vessel wall and calcified plaque, were measured using OCE. The initial Young modulus was 20 and 24 GPa. The maximal stress at the boundary between vessel wall and calcified plaque was 15.4 atm.

Additional decrease of the artery compliance was obtained by creation of crosslinks between fibers of collagen and elastin in the calcified plaques using injection of 0.1% riboflavin and irradiation with UVA light (350-400 nm) of intensity of 3 $mW/cm^2$ for 2 minutes.

The artery compliance was measured using the OCT catheter. The artery cross-section areas were measured under the pressure range from 40 to 200 mm Hg. The compliance measured at 140/90 mm Hg was in the range of 3.6-5.4% 100 mm Hg.

The laser-assisted formation of the porous structure was carried out using a laser system including two laser sources, detecting and modulating system, delivered implement, a catheter, optical fiber and three detecting elements. The laser system was inserted into the artery to be treated. Spatial and temporal modulation was carried out by adjusting the laser wavelength, power, pulse duration and repetition rate using a remote computer as a controller. Two laser sources were used (i) a OPOTEK laser with an adjustable wavelength of 410-2500 nm, an adjustable laser spot diameter of 0.1-2 mm, an adjustable pulse duration of 5-7 ns, and a pulse repetition rate of 10 Hz, and (ii) a 1560 nm diode laser with an adjustable pulse duration of 1-200 ms, an adjustable pulse repetition rate of 1-100 Hz, and adjustable laser spot diameter of 50-600 μm.

An initial laser working condition were established on the base of the solution of inverse math problems concerning heating, thermo-expansion, thermo-mechanical stress propagation, chemical bond breaking, stress relaxation dynamics, formation and development of gas nanobubbles and denaturation micro zones as outlined above. The following parameters have been adjusted: laser wavelength, pulse duration, pulse repetition rate, energy of pulses, duration of one series (number of pulses per a series), interval duration between series, total duration of effect (number of series), dimensions of an area exposed the laser illumination, distance between neighboring areas exposed to the laser illumination. The calculations shown that laser with a wavelength of 1450 nm, pulse duration of 6 ns, pulse energy of 3 mJ, laser spot radius of 0.2 mm, pulse repetition rate of 10 Hz, time exposure 10 of s, facilitated a generation of nanobubbles of 400-1000 nm, and dens of 200-600 nm in diameter.

A feedback controller and the detecting element comprising three types of detecting element (i) detection of backscattering of laser radiation, (ii) detection of electrical conductivity, and (iii) detection of optoacoustic (OA) signals was used to measure temperature increment and to establish formation of nano gas bubbles, micropores and micro-dens.

The sensitivity and resolution of these non-invasive methods were proved using SEM, TEM, SIM, OA microscopy, and Raman spectroscopy.

The feedback control facilitated adjusting the laser parameters during laser treatment and stopping the irradiation when a predetermined threshold was achieved.

In 5 s of irradiation with 6 ns laser pulses, the laser source was changed. For a calcified plaque with average thickness of 0.8 mm, subsequent irradiation with a diode laser operating at the same wavelength of 1450 nm was performed with 10 ms pulses, operating 8 pulses in a series with an interval between series of 6 s. The total time of irradiation was 28 s. The maximal temperature at the boundary between the vessel wall and the calcified plaque was 46° C.

For the calcified plaque with average thickness of 1.9 mm, subsequent irradiation with a diode laser operating at a wavelength of 1450 nm was performed with 10 ms pulses, operating 10 pulses in a series with an interval between series of 10 s. The total time of irradiation was 34 s. The maximal temperature at the boundary between the vessel wall and the calcified plaque was 48° C.

After the laser treatment, the presence of the gas bubbles agglomerating 0.5-3 μm in size, and zones of broken cross-links and denatured collagen fibers of 1-5 μm in size was demonstrated (using confocal two photon exited fluorescence and second harmonic generation microcopy). The stress at the interface between the vessel wall and the calcified plaque (measured with OCE) diminished by 30-50%. The compliance was in the range of 7.0-9.8% 100 mm Hg that is 70-90% higher than before laser treatment.

Then the arteries samples were frozen, and six months later slowly (within 8 hours) thawed to check the stability of the effects obtained. The compliance of the artery was 6.0-8.2% 100 mm Hg. The laser-induced formation of pores of the micron and submicron sizes has made the effect of increasing compliance permanent due to the stabilization of small microbubbles by calcium ions, which tend to accumulate on the surface of microbubbles and their agglomerates. The repulsion of calcium ions prevents their constriction and stabilizes the pores.

The presence of the porous structure including micropores and gas bubble agglomerates of 0.5-3 μm in size was established using confocal microcopy and structured illumination microscopy.

The stability of the positive effect was achieved by the formation of gas ($CO_2$) nanobubbles whose long-term stability was provided by positive ions ($Ca^{++}$) covering the bubble surface at moderate temperatures (below 60° C.). To prove the effect of $Ca^{++}$ ions, the marker Fluo-4 Ca dye (Thermo Fisher Scientific, USA) was applied. Images were obtained with the super-resolution microscope, the optical microscopy experimental system v3.0 (Applied Precision, Inc., the GE Healthcare company). A 532 nm laser was used for the fluorescence excitation, and the objective immersion oil with the refractive index of 1.514. Super-resolution fluorescence images were reconstructed using softWoRx 2.0 (Applied Precision, Inc.). The images clearly demonstrated white colored calcium layers covering the surfaces of microporous structure and gas bubbles agglomerates, as is shown in FIG. 9*b*.

Thus, this ex-vivo experiment demonstrated the formation of microdefects (microporous structure, zones of denaturized tissue, bubbles, and their agglomerates) in the calcified plaques under laser radiation with controlled spatial and temporal modulation instead of macro fracturing of calcified plaques. These microdefects destruct abnormal collagen fibers and crosslinks at the boundary between the calcified plaque and the vessel wall, resulting in stress relaxation and increased compliance of the artery.

Second Example

Before Treatment

The patient had a history of the hypertension, moderate obstruction for the left leg and severe obstruction for the right leg. During life, this patient gave written informed consent for the use of his body for educational and research purposes after death. A selective angiogram of the superficial femoral artery showed CTO in the right femoral popliteal artery above the knee with a length of 4+/−0.5 mm and a highly calcified lesion.

The cross-sectional area of the artery was measured using IVUS. The diameter of the artery above the knee was 6.2+/−0.5 mm with mixed calcified plaque and varying levels of calcification, including a length of 4.3 mm and a highly calcified lesion. Images were acquired using an Eagle Eye Platinum catheter with a 2.5 mm tip.

Frequency domain of the OCT system provides the volumetric images, acquired at the rate of 40 frames per second. The reconstruction time was about 0.5 second. The OCT identified the collagen within the lumen area as uniformly back-scattering region, and microcalcifications within the CTO as highly reflective dots with specific shadows. The OCT demonstrated an extensively calcified wall and dense collagen occupying the lumen area. The wall thickness was 0.48+/−0.02 mm, the thickness of the calcified plaque below CTO was 1.4+/−0.5 mm, therefore the roughness of calcified layer was about 1 mm Laser Treatment The laser system according to the present disclosure with a balloon was used for the treatment of chronic total occlusions (CTO). The diameter of the balloon was 3 mm.

The cold lithotripsy was used to treat the CTO. It was controlled by thermomechanical stress due to the temperature gradients that arise between zones with different content of water due to different porosities of the calcified plaques absorbing laser radiation of 1550 nm in wavelengths. Areas with different contents of water in calcified plaques are formed by the following dosimetry of laser radiation: a wavelength of 1550 nm, a pulse duration of 10 ms, a frequency of 10 Hz, an optical fiber diameter of 600 mm, an exposure time was set by the control system based on real-time detecting information pertaining to the sizes of pores and calculations of the tissue denaturation dynamics to prevent damage of the vessel walls due to long propagation of the porous structure formation and formation of zones of denaturized tissues. The dimensions of the pores were measured during laser treatment by the OCT. The final length was 4.2+/−0.2 mm, the maximal width was 3.0 mm, an average ablation rate was 1.5 mg/s.

Then the molding of the calcified plaque was proceeded in two stages. First porous structure formation on the calcified plaque along the 30 mm length of the vessel walls was achieved with the laser system. The detected information was based on OCT measurements of the pore size during irradiation with a pulse duration of 100 ms and a frequency of 10 Hz. The system performed three series of six pulses in each spot, with a distance between laser spots of 3 mm. The average laser power gradually decreased by the feedback controller from 2.5 to 1.8 W during the exposure time of 3 minutes. At the second stage, a balloon was used to expand the lumen area. The pressure in the balloon was increased to 12 atm for 2 minutes. Then the balloon was partially deflated and shifted to a deeper zone of the arteries, and the laser irradiation was repeated, followed by inflation of the balloon to 12 atm.

After Laser Treatment

The OCT demonstrated a fine long crack within the CTO, an increase in the average lumen diameter from 2.5 to 3.6 mm and a smoothing of the calcified plaque in the rest of the artery. The average roughness of the calcified plaque decreased from 1 to 0.2 mm Therefore, this example demonstrated how effective cold lithotripsy and laser molding are in the treatment CTO and highly calcified lesions of peripheral arteries to increase the lumen area and decrease the roughness of the calcified vessel walls. The developed theoretical model makes it possible to predict the optimal laser dosimetry for such a procedure, and the real-time feedback guarantees effective and safe laser treatment.

Third Example

Before Treatment

The surgical preparation was carried out analogously to the first example. The atherosclerotic changes in the iliac arteries of two pigs were modeled by the diabetic/hypercholesterolemic (DM/HC) method. The presence and size of the calcified plaques in the artery were determined 6 months after the induction of DM/HC using computed tomography and IVUS. The diameter of the arteries was 4.9±0.3 mm, the thickness of the vessel wall was 410±10 μm, the thickness of the calcified plaque was 0.9±0.3 mm. The maximal stress at the boundary between vessel wall and calcified plaque was 12.5 atm. Compliance measured was 6.8+/−3 $mm^2/mmHg\times10^{-3}$. The lumen area was measured every forty milliseconds by means of a 30 MHz intravascular ultrasound catheter and an automatic edge detection program. Simultaneous high-precision pressure measurements were obtained by means of a catheter-tipped pressure microtransducer positioned at the origin of the iliac artery. The slope of the area/pressure regression line was defined as an index of arterial compliance.

Laser Treatment

The initial laser settings were established on the base of the solution of inverse math problem considering heating, thermo-expansion, thermo-mechanical stress propagation, chemical bond breaking, stress relaxation dynamics, formation, and development of denaturation micro zones. The following parameters have been varied: laser wavelength, pulse duration, pulse repetition rate, energy of pulses, duration of one series (number of pulses per a series), interval duration between series, total duration of effect (number of series), dimensions of a region exposed to effect, distance between neighboring regions exposed to effect. The calculations shown that laser wavelength of 2010 nm, pulse duration 1 ms, pulse energy 0.2 J, laser spot 0.4 mm, pulse repetition rate 25 Hz, six pulses in a series, the interval between series of 5 s, allow to get thermomechanical stress of 20-40 atm, micropores of 0.5-3.0 μm, and zones of denaturized tissue less than 3 μm in size.

A balloon of 3 mm in diameter with device catheter maintaining optical fiber and sensors of the diagnostic and control systems was inserted into the artery. The laser system began to work with the initial parameters, which were adjusted by the controller based on real-time measurements and calculations of temperature dynamics and micropores sizes. After 26 s of irradiation, the feedback controller automatically adjusted the laser parameters, and the laser system continued irradiation with a pulse duration of 200 ms, a pulse repetition rate of 2 Hz, a pulse energy of 1.2 J.

The irradiation was stopped after 42 s, when the size of the porous structure with a pore size of 1-5 μm reached 50% of the laser spot size, and the Young's modulus of the calcified plaques decreased from 22 GPa to 10 GPa. The temperature distribution was measured during laser irradiation to prove that the maximal temperature did not exceed 60° C., which ensured the stability of the positive effect of laser induced stress relaxation. Then the optical fiber was automatically shifted by 3 mm along the artery, and all the above operations were repeated for the next zone. A total of 5 zones were irradiated over 21 mm in the artery. The total time of laser exposure was 5 minutes 40 s. At the next stage, the pressure in the inflated balloon was increased to 10 atm for 3 minutes.

After Laser Treatment

The following characteristics of the artery were measured immediately and in six months after laser treatment: The thickness of the calcified plaque and the artery compliance are presented in the Table 1

TABLE 1

| Characteristics | Before treatment | Immediately after treatment | Six months after treatment |
|---|---|---|---|
| Lumen diameter, mm | 3.2 +/− 0.3 | 4.0 +/− 0.2 | 3.8 +/− 0.2 |
| Thickness of a calcified plaque, mm | 0.9 +/− 0.3 mm | 0.5 +/− 0.1 mm | 0.6 +/− 0.1 mm |
| Roughness of a calcified plaque, μm | 450 | 120 | 140 |
| Maximal pressure in the zone between plaque and vessel wall, atm | 12 | 1.4 | 2.5 |
| Young's modulus, GPa | 20 | 7 | 9 |
| Compliance, $mm^2/mmHg \times 10^{-3}$ | 6.8 +/− 3 | 21.6 +/− 2 | 17.2 +/− 2 |

The dynamics of temperature field, and stress distribution was monitored in real-time with OCE and OA methods. The temperature rage 45-58° C. provides stabilization of structural microdefects.

The doppler US examination after treatment demonstrated a normal blood flow velocity of 1.1+/−0.2 m/s.

Examination after twelve months demonstrated the stability of the positive effect achieved as a result of laser treatment. CT did not reveal visible recalcification and restenosis of the vessel wall near the edge of the stent. The doppler ultrasound revealed patency of the implanted stent with normal flow (peak systolic velocity of 1.3+/−0.2 m/sec).

Thus, this example shows how the molding of the calcified plaque under the combined effect of thermomechanical action of laser radiation, which produces micropores, and an inflated balloon can significantly increase compliance and that this positive effect persists for at least 6 months. The harmful effect of the mechanical stress on the boundary of the vessel walls was eliminated by the laser-induced stress relaxation. This example demonstrated the stability of stress redistribution in-vivo due to laser induced stress relaxation in calcified blood vessel. The laser system used multiple detecting elements and fast real-time data processing by a remote quantum computer to ensure the safety and efficacy of laser treatment.

Fourth Example

The patient was 62 years old. The doppler ultrasound showed sub-occlusion of the left common iliac artery with a significant acceleration of blood flow (4.9+/−0.4 m/sec). The CT showed a vessel diameter of 8.6 mm and atherosclerotic lesion 82 mm in length. The standard stenting procedure was performed under fluoroscopic guidance, the patient was consciously sedated, and 2% lidocaine was used as a local anesthetic. The Epic Vascular Self-Expanding Stent System (Boston Scientific, USA) was used. A 9-mm-diameter balloon-expandable stent was introduced through an 8-F guiding catheter.

Then the instrument of the laser system was introduced into the vessel through the catheter. The residue stress in the vessel wall near the edge of the stent measured using OCE was 1.9 atm (192 kPa) which is five times higher than the normal stress at the vessel wall.

The remote computer established the laser dosimetry for stress relaxation: a laser wavelength of 1060 nm, a power of 5.4 W, a pulse duration of 1 ms, a pulse repetition rate of 20 Hz. The residue stress was measured during irradiation with the OCE. The feedback controller controlled the laser power during treatment and stopped the laser when the residue stress diminished to 0.35 atm (35 kPa)—a normal stress in the artery wall. The total irradiation time was 170 s.

Thus, this example shows that laser relaxation of residue stress makes it possible to prevent recalcification and restenosis of the artery after stenting. The laser system with a feedback control and a remote high-performance computer makes the positive effect stable for a long time.

Laser elimination of residue stress can be the final procedure for stenting and other types of treatment of calcified arteries. Removal of residue stress is an important procedure which diminish secondary effect and long-term biological response of the arteries after any treatment, accompanied by plastic deformation.

The description of the specific embodiments and the Figures merely serve to illustrate the techniques of the present disclosure and the advantageous effects associated therewith but should not imply any limitation. The scope of the disclosure is to be inferred from the appended claims.

Although this disclosure addresses a calcified plaque in the blood vessel or at the vessel wall as an example, it is understood that the in-vivo object may refer to any other object in a blood vessel, for example an object whose volume should be reduced in the blood vessel, or whose mechanical stress should be relaxed.

In the context of the present disclosure, a porous structure may refer to a structure with a distributed plurality of structural defects. A pore in such a porous structure does not need to be of a rounded shape as in a conventional sense, but can also be a crack, creek, cavity, displacement, or another form of a structural defect. Yet a porous structure should also be distinguished from an assemble of fractures, wherein a porous structure may still be essentially intact on a macroscopic level. In an exemplary configuration, the porous structure may be a microporous structure. That is to say, the majority of the structural defects in this configuration can have the size less than 5 micrometers. At an initial stage of formation of such a microporous structure, the formation may only modify the physical properties of the affected area and may not significantly change the macroscopic appearance.

In some embodiments, the in-vivo object may already be porous before the laser induced porous formation. In these embodiments, a porous structure refers to a structure with an increased porosity over the untreated in-vivo object. In some embodiments, a porous structure formation may refer to an increase in the porosity and/or an increase in the pore sizes. This makes it possible to control the mechanical properties of calcified plaques, in particular their tensile strength and yield strength.

In the context of the present disclosure, "real-time" may generally refer to a time scale in which the one or more physical, chemical, mechanical and/or dimensional characteristics of the area of the in-vivo object are detected from the area of the in-vivo object undergoing modification and are subsequently processed, wherein the time scale is sufficiently short to allow the dosimetry of the laser source to be purposefully regulated by way of feedback based on the detected and processed information during the ongoing modification of the calcified blood vessel.

In the context of the present disclosure, "real-time" may refer to a time scale smaller than several minutes. For example, detecting in real-time may refer to detecting continuously over a time period of several minutes or detecting several minutes after an external effect for evaluation of such effect. Processing in real-time may refer to a processing where the result can be calculated several minutes after the calculation starts. Nonetheless, a smaller time scale is likewise possible.

In particular, real-time may refer to a time scale smaller than 10 minutes, in particular smaller than 5 minutes or smaller than 3 minutes or smaller than 1 minute or smaller than 30 seconds or smaller than 10 seconds or smaller than 1 second.

In the context of the present disclosure, "regulating a dosimetry of a laser" or "regulating a laser" may refer to regulating the laser in operation. However, they may also comprise selecting a proper initial parameter of the laser for starting the laser treatment. In that case, detecting in real-time may refer to the situation where the characteristics are detected within a time span of up to several minutes before the laser starts to work. The laser may be started in different initial conditions depending on the exact situation of the to-be-treated blood vessel.

In an implementation of the laser system of the first aspect, the laser may be regulated by adjusting at least one of the following laser parameters: a laser pulse repetition rate; a duration of a laser pulse; a shape of a laser signal in the time domain; a shape of the laser signal in the frequency domain; a laser wavelength; a pulse energy; an intensity of the laser signal; a number of pulses in a pulse series; an interval duration between series; a number of total series; a spatial distribution of laser irradiation intensity; a dimension of irradiated area; a distance between neighboring irradiated areas; and a distance shift due to the propagation in the first optical delivery element.

Adjusting one or more of these parameters may facilitate a fine tuning based on the environment properties, which may increase the precision of the laser light modulation and the range of applications.

In a further implementation of the laser system of the first aspect, the detecting element may comprise at least one of the following: an X-Ray device; a CT device; an ultrasonography device (US); a Doppler US device; an MRI device; an Intravascular ultrasound device (IVUS); an OCT device; a (multispectral) optoacoustic tomography device (MSOT); a fluorescence molecular tomography device (FMT); and an acoustic tomography device.

These types of detecting elements may provide high resolution monitoring of the in-vivo object or a local environment but may generate a large volume of data. Through combining a plurality of different types of the detecting elements with a powerful (built-in or external) computer, for example a quantum computer, the disclosure may facilitate a precise real time control of the laser regulation.

In a further implementation of the laser system of the first aspect, the detecting element may be an optical coherent elastography equipment, and/or an optoacoustic diagnostic device.

The OCE and/or an optoacoustic diagnostic device may facilitate a real-time high-resolution detection of mechanical stress on the in-vivo object or in the environment. This may increase the precision of the laser light modulation.

In the context of the present disclosure, any characteristic relating to the area of the in-vivo object or the in-vivo object itself that allows to derive information to assess the state of the in-vivo object for a subsequent modification of the in-vivo object in a feedback loop may be considered a physical, chemical, mechanical and/or dimensional characteristic of the area of the in-vivo object.

In particular, the dimensional characteristic may relate to a size and/or shape of the (area of the) in-vivo object and/or a size of the pores and/or size of the denatured area.

In a further implementation of the laser system the one or more physical, chemical, mechanical and/or dimensional characteristics may comprise one of the following: a position of the in-vivo object; a composition of the in-vivo object; a dimension of the in-vivo object; a temperature of the in-vivo object and/or of the environment of the in-vivo object; a stress distribution of the area of the in-vivo object; a stress distribution near a vessel wall of the blood vessel; a light scattering induced by the in-vivo object area; a conductivity of the in-vivo object; a Young's modulus of the in-vivo object area; a characteristic pertaining to a porous structure and/or a zone of denaturized tissue on the in-vivo object; a lumen area of the blood vessel; a compliance of the blood vessel; a strength of the in-vivo object; and a plasticity threshold of the in-vivo object.

In a further implementation of the laser system of the first aspect, the laser system may comprise a servo element.

In a further implementation of the laser system of the first aspect, the servo element may be configured to change the position of the detected area of the detecting element, the position of the first optical delivery element and/or the position of the catheter.

This may facilitate a spatial resolved distribution information, which may provide more information for the feedback controller, which may increase the precision of the laser light modulation.

In a further implementation of the laser system of the first aspect, the feedback controller may be configured to control a distance between the catheter and the in-vivo object in the course of the irradiation based on the real-time-detected information.

This may facilitate a change of the illuminated area during the laser treatment.

In a further implementation of the laser system of the first aspect, the detecting element may comprise an optical receiving element.

In a further implementation of the laser system of the first aspect, the optical receiving element may be configured to receive a scattered light.

The scattered light may stem from the spatially and/or temporally modulated laser light. Light scattering may be sensitive to the formation of microporous structures, or other defects on a microscopic level. Detecting and analyzing scattered light of different wavelengths makes it possible to use the Mie and Rayleigh scattering laws, to determine the size distributions of pores or defects in the in-vivo object or potential gas bubbles, which may be generated during the porous structure formation.

In a further implementation of the laser system of the first aspect, the detecting element may comprise a second optical delivery element.

In a further implementation of the laser system of the first aspect, the optical delivery element may be configured to deliver a probing light signal for light scattering analysis.

Scattered light may also stem from a probing light signal. The probing light signal need not interact with the in-vivo object so as to form pores or tissue denaturation and can be used before the laser operation to determine the initial condition of the laser. This may facilitate an initial condition of the laser with little or no destructive side effect on the in-vivo object or its environment.

In a further implementation of the laser system of the first aspect, the first optical delivery element comprises a bundle of optical fibers and/or is configured to multiplex a plurality of laser outputs of the laser source into one fiber at an input of the first optical delivery element.

This may improve a flexibility of the spatial modulation of the laser light as well as the scattered light detection mentioned above.

In a further implementation of the laser system of the first aspect, the detecting element may comprise a conductivity detecting element.

In a further implementation of the laser system of the first aspect, the conductivity detecting element may be configured to detect a conductivity on the vessel wall.

In some embodiments, it may be beneficial to form a stabilized porous structure. This can be realized through a stabilized gas bubbles generation. A spatial and/or temporal modulated laser light is capable of generating microbubbles from gas dissolved from the liquid in the environment. These bubbles may be stabilized by positive charges on their surfaces. The conductivity information may therefore reflect the status of the bubble formation. Modulating the laser light considering this information may facilitate a controlled generation of stabilized gas bubbles. It may further facilitate a controlled formation of stabilized porous structure.

In a further implementation of the laser system of the first aspect, the laser system may comprise a balloon.

In a further implementation of the laser system of the first aspect, the balloon may be configured to be inflated and/or deflated in the blood vessel.

In a further implementation of the laser system of the first aspect, the feedback controller may be further configured to control the gas pressure in the balloon, and/or to implement a desired positioning of the balloon in real-time based on the real-time detected information.

In some embodiments where a balloon is used, the disclosure may facilitate an optimization in controlling the balloon, which may reduce the pressure needed for the balloon and thus may reduce the destructive effect on the blood vessel.

In a further implementation of the laser system of the first aspect, the feedback controller may comprise or may be coupled to a (remote) high-performance computer, a (remote) hybrid quantum-classical computational facility, and/or a (remote) quantum computer.

In a further implementation of the laser system of the first aspect, the feedback controller may comprise and/or may be connected to a storage device, the storage device storing an offline settings table for the treatment, wherein the setting table is calculated by a remote high-performance computer, a remote hybrid quantum-classical computational facility, and/or a remote quantum computer.

The real-time regulation of the laser based on feedbacked detected information of the laser affected area according to the present disclosure is a complex feedback optimization problem. A better evaluation of the laser effect and a precise regulation of the laser relies on a large volume of detected information, which is of multiple dimensions. Quantum algorithms or hybrid-quantum algorithms such as a variational quantum eigensolvers may be employed in this context and may outperform a conventional algorithm in optimizing a system with parameters of multiple dimensions. Therefore, using a quantum-computer and/or a hybrid computational facility may facilitate a better control of the laser system.

A second aspect of the disclosure provides a method for detecting and processing information, comprising:

a) detecting one or more physical, chemical, mechanical and/or dimensional characteristics of an area of an in-vivo object in a calcified blood vessel; and
b) processing the detected information pertaining to the physical, chemical, mechanical and/or dimensional characteristics to acquire a property of a porous structure and/or a zone of denaturized tissue in the in-vivo object.

A property of a porous structure and/or a zone of denaturized tissue on the in-vivo object may refer to a pore size, a stability, a quality, or a property used for an evaluation of the porous structure and/or the zone of denaturized tissue in the in-vivo object.

In an implementation of the method of the second aspect, the detected information pertaining to the physical, chemical, mechanical and/or dimensional characteristics of the area of the in-vivo object may be processed to acquire a property of a porous structure formation and/or a formation of a zone of denaturized tissue in the in-vivo object.

A property of a porous structure formation and/or a formation of a zone of denaturized tissue in the in-vivo object may refer to a formation speed, a stability, a quality, or a property used for evaluation of the porous structure formation and/or the formation of a zone of denaturized tissue in the in-vivo object.

In a further implementation of the method of the second aspect, the detected information pertaining to the physical, chemical, mechanical and/or dimensional characteristics of the area of the in-vivo object may be detected in real-time during the porous structure formation and/or a formation of a zone of denaturized tissue.

In a further implementation of the method of the second aspect, the porous structure formation and/or the formation of the zone of denaturized tissue may be induced by a temporally and/or spatially modulated laser light generated by a laser source.

Different porous structure formation mechanisms may require different temperatures. The temperature may reflect which kind of porous structure is formed, for example whether the porous structure formed is temporal or stabilized. Monitoring a stress distribution may reveal the fraction of the stress that has already been reduced and the fraction of the stress that still has to be reduced. It may also provide an information on a size distribution of the pores or the denaturized tissues in the porous structure or the zone of denaturized tissue. In addition, a mechanical stress of the in-vivo object need not be an internal mechanical stress. A stress may also arise in the area of the in-vivo object due to the temperature gradient in this area which may be generated by the laser. For example, a detected stress may be mapped to the detected temperature, since it may provide a more precise evaluation of the laser irradiation effect. The combination of the temperature detection and a mechanical stress detection may reflect different aspects of the in-vivo object and may facilitate a precise evaluation of the laser effect. Other physical, chemical, mechanical and/or dimensional characteristics of the area of the in-vivo object may provide information for a better evaluation of the in-vivo object area and a laser effect.

Although the present disclosure may provide an automatic feedback-control laser system, for example the laser system according to the first aspect, it is understood that the method according to the second aspect need not encompass the regulation of laser system itself. For example, the method according to the second aspect can provide the doctor or the practitioner operating a laser with the necessary information based on which the doctor or the practitioner may subsequently evaluate the in-vivo object and/or a laser effect.

An evaluation system, configured to perform the method according to the second aspect may comprise an indicator, for example an indicating LED light bulb. In an example, if the evaluation system determines that the to-be treated blood vessel area shows a high residue stress or comprises a large, calcified plaque, it may indicate the doctor or the practitioner to perform a laser treatment, for example through showing a green light. In another example, if the evaluation system determines that the detected information in the to-be treated blood vessel reaches a predetermined value, for example if a stress is small enough, or a temperature is too high, it may indicate the doctor or the practitioner to stop the laser treatment, for example through showing a red light. The method may also provide indications to the doctor to perform other actions, for example to change the dosimetry of the laser. The threshold, the predetermined value and/or other evaluation criteria may be predetermined by the doctor or the practitioner based on concrete cases, or stored in an offline settings table for the treatment, wherein the setting table may be calculated by a remote high-performance computer, a remote hybrid quantum-classical computational facility, and/or a remote quantum computer. The threshold, the predetermined value and/or other evaluation criteria may be predetermined based on the laser used by the doctor or the practitioner, which may be a laser in the laser system according to the first aspect of the disclosure. The laser may also be a laser where the dosimetry can be adjusted manually.

In a further implementation of the method of the second aspect, the processing of the detected information may comprise generating a value for a dosimetry of the laser source in real-time based on the detected information pertaining to the physical, chemical, mechanical and/or dimensional characteristics of the in-vivo object area.

In an automatic laser system such as the laser system according to the first aspect of the disclosure, the generated value for a dosimetry of the laser may be directly used by the feedback controller to regulate the laser dosimetry without human interference. The value may also be displaced to the doctor or the practitioner, so that they can use it to manually adjust a laser dosimetry or to decide whether to stop the laser treatment. As long as the detecting and the processing of the information can be performed in real-time, for example within several minutes, the doctor or the practitioner may have enough time to react to change the laser dosimetry in time for a real-time laser effect, even if the doctor or the practitioner chooses to change the laser dosimetry manually.

Compared to conventional monitoring and evaluation systems, an evaluation system adopting the method according to the second aspect provides a more informative and precise feedback to the doctor or the practitioner operating a laser system for calcified blood vessel systems.

In a further implementation of the method of the second aspect, the value may be generated in real-time during the porous structure formation and/or the formation of the zone of the denaturized tissue.

In a further implementation of the method of the second aspect, the detecting the physical, chemical, mechanical and/or dimensional characteristics of the area of the in-vivo object in a blood vessel may comprise: detecting a temperature in the area.

In a further implementation of the method of the second aspect, the value for a dosimetry of a laser source may be generated if the temperature is within a predetermined range.

For the laser ablation according to the present disclosure, for the cold lithotripsy, the parameter may be adjusted in such a way that the detected temperature can be maintained above the threshold. This may increase the efficiency of the laser effect and may reduce the waste of energy. It may therefore facilitate an efficient use of resources. For a stabilized porous structure formation, the parameter may be adjusted so that the detected temperature can be maintained below the threshold, within a predetermined range. The gas bubbles can be stabilized in a lower temperature range. In an exemplary configuration, the threshold may be determined to be a value no smaller than 40° C. and/or no larger than 90° C.

In a further implementation of the method of the second aspect, the physical, chemical, mechanical and/or dimensional characteristics may comprise a characteristic of a scattered light.

In a further implementation of the method of the second aspect, the processing of the detected information may further comprise calculating a pore size distribution of the porous structure based on the scattered light.

The pore size distribution of the porous structure may be used to determine the water content in this area. The knowledge of the water content may be used for modulating the laser light to increase the thermomechanical stress and ablation efficiency.

In a further implementation of the method of the second aspect, the generating of the value for a dosimetry of a laser source may comprise generating a time interval between two laser pulses to be longer than a time it takes for a fluid to fill the porous structure after a porous structure formation.

The fluid can be blood, or water, or any other biological fluid in the environment of the laser treatment. For a cold lithotripsy, controlling the time interval between two laser pulses may increase the cross section of the interaction between the porous structure filled with the fluid and the laser radiation for every pulse. This may facilitate an efficient use of laser energy.

In a further implementation of the method of the second aspect, the time interval may be generated based on the pore size distribution of the porous structure.

In a further implementation of the method of the second aspect, the processing of the detected information may comprise: analyzing a thermomechanical gradient of the area of the in-vivo object.

In a further implementation of the method of the second aspect, the processing of the detected information may further comprise calculating a stress distribution and/or a temperature distribution in the area of the in-vivo object.

In a further implementation of the method of the second aspect, the processing of the detected information may comprise mapping the stress distribution to the temperature distribution and/or evaluating the correlation between the stress distribution and the temperature distribution.

A spatially resolved distribution may provide more information about the laser effect, which may increase the precision of the laser regulation.

In a further implementation of the method of the second aspect, the method may comprise detecting a physical, chemical, mechanical and/or dimensional characteristic of the area of the in-vivo object in the calcified blood vessel before, during and/or after the porous structure formation and/or the formation of a zone of denaturized tissue in the in-vivo object.

In a further implementation of the method of the second aspect, the method may comprise processing the detected information pertaining to the physical, chemical, mechanical and/or dimensional characteristics of the area of the in-vivo object in the calcified blood vessel before and/or after the porous structure formation and/or the formation of a zone of denaturized tissue in the in-vivo object to identify a location where a stress is higher than a predetermined value.

This location may correspond to the area needed to be treated or the location with residue stress. For example, laser radiation can be used on this location for generating porous structure to reduce the stress.

In a further implementation of the method of the second aspect, the in-vivo object may be a blood vessel wall.

In a further implementation of the method of the second aspect, the method may further comprise detecting a physical, chemical, mechanical and/or dimensional characteristic of the area of an in-vivo object on the blood vessel wall before and/or after the blood vessel wall has undergone a mechanical action.

Examining a residue stress on a blood vessel wall and relaxing it for example through a laser treatment may reduce the chance of recalcification and restenosis of the blood vessel and/or the risk of future operation. This may increase effectively the per-operation output of the laser radiation and may optimize the use of resources. The mechanical action may be generated by an expanded balloon, an inserted stent or by the thermomechanical effect of laser radiation in the course of another treatment step performed on the blood vessel.

In a further implementation of the method of the second aspect, the laser may be configured to generate gas bubbles from gas molecules dissolved in a liquid in the blood vessel.

This may facilitate formation of a stabilized microporous structure, which may reduce the stress on the in-vivo object without destroying it.

In a further implementation of the method of the second aspect, the processing of the detected information may be performed in a (built-in or remote) high-performance computer, a (built-in or remote) hybrid quantum-classical computational facility, and/or a (built-in or remote) quantum computer.

In a further implementation of the method of the second aspect, the method of the second aspect may be encompassed in an algorithm designed for the high-performance computer, the hybrid quantum-classical computational facility, and/or the quantum computer.

In a further implementation of the method of the second aspect, the remote high-performance computer, the remote hybrid quantum-classical computational facility, and/or the remote quantum computer may be located in a central server.

In a further implementation of the method of the second aspect, the central server is configured to regulate a plurality of laser systems.

A third aspect of the disclosure provides a method for treating a calcified blood vessel using a temporal and/or spatial modulated laser light comprising a treatment step, wherein the treatment step comprises:

a) detecting one or more physical, chemical, mechanical and/or dimensional characteristics of an area of an in-vivo object in the vessel, and feedbacking the detected information pertaining to the physical, chemical, mechanical and/or dimensional characteristics in real-time to a feedback controller; and
b) modulating the laser light in real-time by the feedback controller based on the detected information, the modulating suitable for a controlled formation of a porous structure and/or a zone of denaturized tissue in the in-vivo object.

In an implementation of the method of the third aspect, the modulating the laser light in real-time may further comprise disrupting the laser when the value of the detected information achieves a predefined threshold or is located within a predefined range.

In a further implementation of the method of the third aspect, the method may comprise a first step of diagnosing the vessel and corresponding tuning of the necessary initial laser radiation parameters; a second step of treating a calcified plaque in the vessel; and/or a third step of treating a vessel wall, after the second step is concluded.

In a further implementation of the method of the third aspect, at least one of the second or third step may comprise the treatment step.

In a further implementation of the method of the third aspect, all three steps may comprise a method of the second aspect of the disclosure.

In the present disclosure, the numbering of steps may distinguish different steps. It need not impose a sequence in which the steps should be carried out. For example, a first step of diagnosing the vessel may also be carried out after a third step is concluded to evaluate the third step.

In a further implementation of the method of the third aspect, the method may comprise a fourth step of expanding a vessel lumen area after the porous structure and/or the zone where the denaturized tissue is formed in the in-vivo object in the treatment step.

In a further implementation of the method of the third aspect, the expanding a vessel lumen area may be realized through a balloon and/or a stent.

In a further implementation of the method of the third aspect, the pressure to be exerted by the balloon and/or a stent may be determined by the feedback controller.

A fourth aspect of the disclosure provides a method for increasing lumen area and compliance of atherosclerotic cardio vessels, comprising:

a) detecting information about atherosclerotic cardio vessels, including a stress distribution, a plaque position, configuration, composition and dimensions, Young's modulus, and compliance of the arteries;
b) processing the detected information by a computational algorithm to define an initial laser dosimetry for treatment of atherosclerotic cardio vessels, including softening and molding the calcified plaque, stress relaxation, cold lithotripsy of chronic total occlusions; and
c) laser irradiation of atherosclerotic cardio vessels to produce a softening and molding of the calcified plaque, and stress relaxation in atherosclerotic cardio vessels, and cold lithotripsy of the chronic total occlusions.

In an implementation of the method of the fourth aspect, the various operational procedures may include, but not restricted to, stress relaxation, creating microdefects, microcracking, molding, and cold lithotripsy resulting from the effect of the spatial and temporal modulated laser beam. They may be applied simultaneously or step by step in various combination.

In a further implementation of the method of the fourth aspect, the softening and molding of the calcified plaque, and/or the stress relaxation, and/or the cold lithotripsy of the chronic total occlusions may be produced due to formation of porous structure and/or the formation of the zone of denaturized tissue as induced by a temporal and/or spatial modulated laser light, and the parameters may be adjusted in real-time during increasing lumen area and compliance of the vessels due to stress relaxation, the porous structure formation and/or the formation of the zone of denaturized tissue.

In a further implementation of the method of the fourth aspect, the molding of calcified arteries may be produced by softening the calcium plaque followed by a mechanical action on the calcified vessels, wherein the mechanical action may be achieved by the inflation of a balloon inserted into the calcified vessels and using a thermo-mechanical effect induced by the spatially modulated laser radiation.

In a further implementation of the method of the fourth aspect, the detecting a temperature and a stress of the area of the in-vivo object in a blood vessel may comprises detecting a temperature distribution and a stress distribution of the area of the in-vivo object; and detecting and relaxation of the residual stress after the molding and/or cold lithotripsy procedures.

In a further implementation of the method of the fourth aspect, the processing of the detected information further may further comprise calculating temperature and stress distributions, and pore size distribution in the area of the in-vivo object.

In a further implementation of the method of the fourth aspect, the adjusting of the parameter may comprise adjusting a time interval between two laser pulses to be longer than a time it takes for the water to fill the porous structure.

In a further implementation of the method of the fourth aspect, the stabilization of a residual stress in the vessel wall may be controlled by establishing the optimal temperatures achieved in the course of the final stage of the laser treatment.

In a further implementation of the method of the fourth aspect, a laser generation of the structural microdefects, including micropores in the plaques may be used to enhance the delivery of drugs to the vessel walls through the calcium-fibrous formations to prevent recalcification and restenosis of the arteries.

A fifth aspect of the disclosure provides a method for detecting and processing information, comprising:

a) detecting a physical-chemical, mechanical and/or dimensional characteristics of an area of an in-vivo object in a calcified blood vessel;

b) processing the detected information pertaining to the physical-chemical, mechanical and/or dimensional characteristic of the in-vivo object area to modify vital features of the vessel, a compliance, strength and plasticity threshold, lumen area of the blood vessel and the stress distribution of the area of the in-vivo object, to acquire a property of a porous structure formation and/or a formation of a zone of denaturized tissue in the in-vivo object, wherein the information pertaining to the physical-chemical, mechanical and/or dimensional characteristics of the in-vivo object area is detected in real-time during the porous structure formation and/or the formation of a zone of denaturized tissue.

In an implementation of the method of the fifth aspect, the method may comprise adjusting a parameter of a laser in real-time based on the detected information pertaining to the characteristics of the in-vivo object area, wherein the porous structure formation and/or the formation of the zone of denaturized tissue is induced by the temporal and/or spatial modulated laser light generated by the laser.

In a further implementation of the method of the fifth aspect, the parameter of the laser may be adjusted simultaneously to, or step by step with the modification of the vital features of the blood vessel, a compliance, strength and plasticity thresholds, lumen area of the blood vessel and the stress distribution of the area of the in-vivo object, porous structure formation and/or the formation of the zone of denaturized tissue.

In a further implementation of the method of the fifth aspect, the method may comprise regulation of strength and plasticity thresholds of the calcified plaque of the blood vessel followed by the mechanical action to modify the shape and roughness of the calcified plaque, wherein the mechanical action is achieved by an inflation of a balloon inserted into the calcified vessels and/or a thermo-mechanical effect induced by the spatially modulated laser light.

In a further implementation of the method of the fifth aspect, the detecting a physical-chemical, mechanical and/or dimensional characteristics of the area of the in-vivo object in the calcified blood vessel may comprise detecting a temperature distribution and a stress distribution of the area of the in-vivo object before and/or during the modification of the lumen area and the compliance of the blood vessel, shape and roughness of the calcified plaque; followed by the detecting the stress distribution in the plaque and vessel wall.

In a further implementation of the method of the fifth aspect, the processing of the detected information may further comprise calculating the temperature distribution, the stress distributions, and/or a pore size distribution in the area of the in-vivo object.

In a further implementation of the method of the fifth aspect, the adjusting of the parameter may comprise adjusting a time interval between two laser pulses to be longer than a time it takes for the water to fill the porous structure.

In a further implementation of the method of the fifth aspect, the parameter of laser may be adjusted to establish a predetermined temperatures on the in-vivo object area during the porous structure formation and/or a formation of a zone of denaturized tissue on the in-vivo object followed by the regulating the stress field in the blood vessel.

In a further implementation of the method of the fifth aspect, the method further comprises delivering a drug to the in-vivo object area, where the porous structure is formed.

All references, including publications, patent applications, and patents, cited herein are hereby incorporated by reference to the same extent as if each reference were individually and specifically indicated to be incorporated by reference and were set forth in its entirety herein.

The use of the terms “a” and “an” and “the” and “at least one” and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A laser system for modification of a calcified blood vessel, comprising:

a laser source;

a feedback controller configured to regulate a dosimetry of the laser source to produce spatially and/or temporally modulated laser light;

a catheter comprising a first optical delivery element adapted to guide the modulated laser light to an in-vivo object in the calcified blood vessel, wherein the in-vivo object includes a calcified plaque; and a detecting element configured to detect one or more physical, chemical, mechanical and/or dimensional characteristics of an area of the in-vivo object in real-time, wherein the feedback controller is configured to process the real-time detected information pertaining to the one or more physical, chemical, mechanical and/or dimensional characteristics of the area in real-time, and wherein the feedback controller is further configured to regulate in real-time the dosimetry of the laser source based on the real-time-detected information for a controlled formation of a microporous structure, essentially intact on a macroscopic scale, in the calcified plaque of the in-vivo object.

2. The laser system of claim 1, wherein the one or more physical, chemical, mechanical and/or dimensional characteristics comprise at least one of:

a position of the in-vivo object;

a composition of the in-vivo object;

a dimension of the in-vivo object;

a temperature of the in-vivo object and/or of an environment of the in-vivo object;

a stress distribution of an area of the in-vivo object;

a stress distribution near a vessel wall of the calcified blood vessel;

a light scattering induced by the area of the in-vivo object;

a conductivity of the in-vivo object;

a Young's modulus of the area of the in-vivo object;

a characteristic pertaining to a porous structure on the in-vivo object;

a lumen area of the blood vessel;

a compliance of the blood vessel;

a strength of the in-vivo object; and a plasticity threshold of the in-vivo object.

3. The laser system of claim 1, wherein the feedback controller is configured to control, based on the real-time detected information, a distance between the optical delivery element and the in-vivo object during an irradiation by the laser source.

4. The laser system of claim 1, wherein the first optical delivery element comprises a bundle of optical fibers and/or is configured to multiplex a plurality of laser outputs of the laser source into one fiber at an input of the first optical delivery element.

5. The laser system of claim 1, further comprising a balloon configured to be inflated and deflated in the calcified blood vessel; wherein the feedback controller is further configured to control a gas pressure in the balloon and/or to implement a desired positioning of the balloon in real-time based on the real-time detected information.

6. The laser system of claim 1, wherein the feedback controller comprises and/or is coupled to a remote high-performance computer, a hybrid quantum-classical computational facility, and/or a quantum computer.

7. The laser system of claim 1, wherein the feedback controller comprises and/or is connected to a storage device, the storage device storing an offline settings table, wherein the settings table is calculated by a remote high-performance computer, a remote hybrid quantum-classical computational facility, and/or a remote quantum computer.

* * * * *